(12) United States Patent
Miura et al.

(10) Patent No.: US 10,976,314 B2
(45) Date of Patent: Apr. 13, 2021

(54) DEVICE, NON-TRANSITORY COMPUTER-READABLE STORAGE MEDIUM, AND METHOD FOR DETERMINING TYPE OF TARGET PEPTIDE

(71) Applicant: SYSMEX CORPORATION, Kobe (JP)

(72) Inventors: Yukiko Miura, Kobe (JP); Hiroyuki Kabata, Kobe (JP)

(73) Assignee: SYSMEX CORPORATION, Kobe (JP)

( * ) Notice: Subject to any disclaimer, the term of this patent is extended or adjusted under 35 U.S.C. 154(b) by 811 days.

(21) Appl. No.: 14/810,980

(22) Filed: Jul. 28, 2015

(65) Prior Publication Data

US 2016/0033500 A1 Feb. 4, 2016

(30) Foreign Application Priority Data

Jul. 29, 2014 (JP) .............................. JP2014-154333

(51) Int. Cl.
*G01N 33/557* (2006.01)
*G16C 20/20* (2019.01)

(52) U.S. Cl.
CPC ........... *G01N 33/557* (2013.01); *G16C 20/20* (2019.02)

(58) Field of Classification Search
None
See application file for complete search history.

(56) References Cited

U.S. PATENT DOCUMENTS 9,880,175 B2 * 1/2018 Mitra ................... G01N 33/582
2005/0026219 A1 2/2005 Hadamovsky et al.
2006/0243899 A1 11/2006 Matsuo et al.

OTHER PUBLICATIONS

Y Kurihara et al. Fabrication of Carboxylated Silicon Nitride Sensor Chips for Detection of Antigen-Antibody Reaction using Microfluidic Reflectrometric Interference Spectroscopy. Langmuir. vol. 28, p. 13609-13615 (Year: 2012).*
Gesellchen et al. "Direct Optical Detection of Protein-Ligand Interactions" In Protein-Ligand Interactions, pp. 17-45. Humana Press (Year: 2005).*

(Continued)

*Primary Examiner* — Oliviva M. Wise
(74) *Attorney, Agent, or Firm* — Sughrue Mion, PLLC

(57) ABSTRACT

Disclosed are devices, programs and methods for determining a type of target peptide contained in a test sample, which relate to comparing first to third information on the target peptide obtained from the test sample with first to third information on a known peptide stored in the storage unit; and determining whether or not the target peptide is the known peptide, wherein the first information is a dissociation rate constant when the target peptide dissociates from a protein, in a solid phase carrier in which the target peptide is immobilized on a support through the protein binding to a peptide, the second information is a maximum value of a layer thickness change amount on the support, and the third information is information indicating that a dissociation mode of a peptide and the protein is either a single dissociation mode or a multiple dissociation mode.

11 Claims, 14 Drawing Sheets

Specification includes a Sequence Listing.

(56) References Cited

OTHER PUBLICATIONS

Bañuls et al. Chemical surface modifications for the development of silicon-based label-free integrated optical (IO) biosensors: A review. Analytica Chimica Acta, vol. 777, p. 1-16 (Year: 2013).*

Bilitewski. Protein-sensing assay formats and devices. Analytica Chimica Acta 2006, vol. 568, pp. 232-247 (Year: 2006).*

Hanel et al. "Comparison of reflectometric interference spectroscopy with other instruments for label-free optical detection", Anal Bioanal Chem, 2002 vol. 372 pp. 91-100 (10 pages total).

Stephan et al. "Binding assay for low molecular weight analytes based on reflectometry of absorbing molecules in porous substrates", The Royal Society of Chemistry, 2014, vol. 139, pp. 1987-1992 (8 pages total).

Piehler et al. "Fast Transient Cytokine-Receptor Interactions Monitored in Real Time by Reflectometric Interference Spectroscopy", Analytical Biochemistry, 2001, vol. 289, pp. 173-186 (14 pages total).

\* cited by examiner

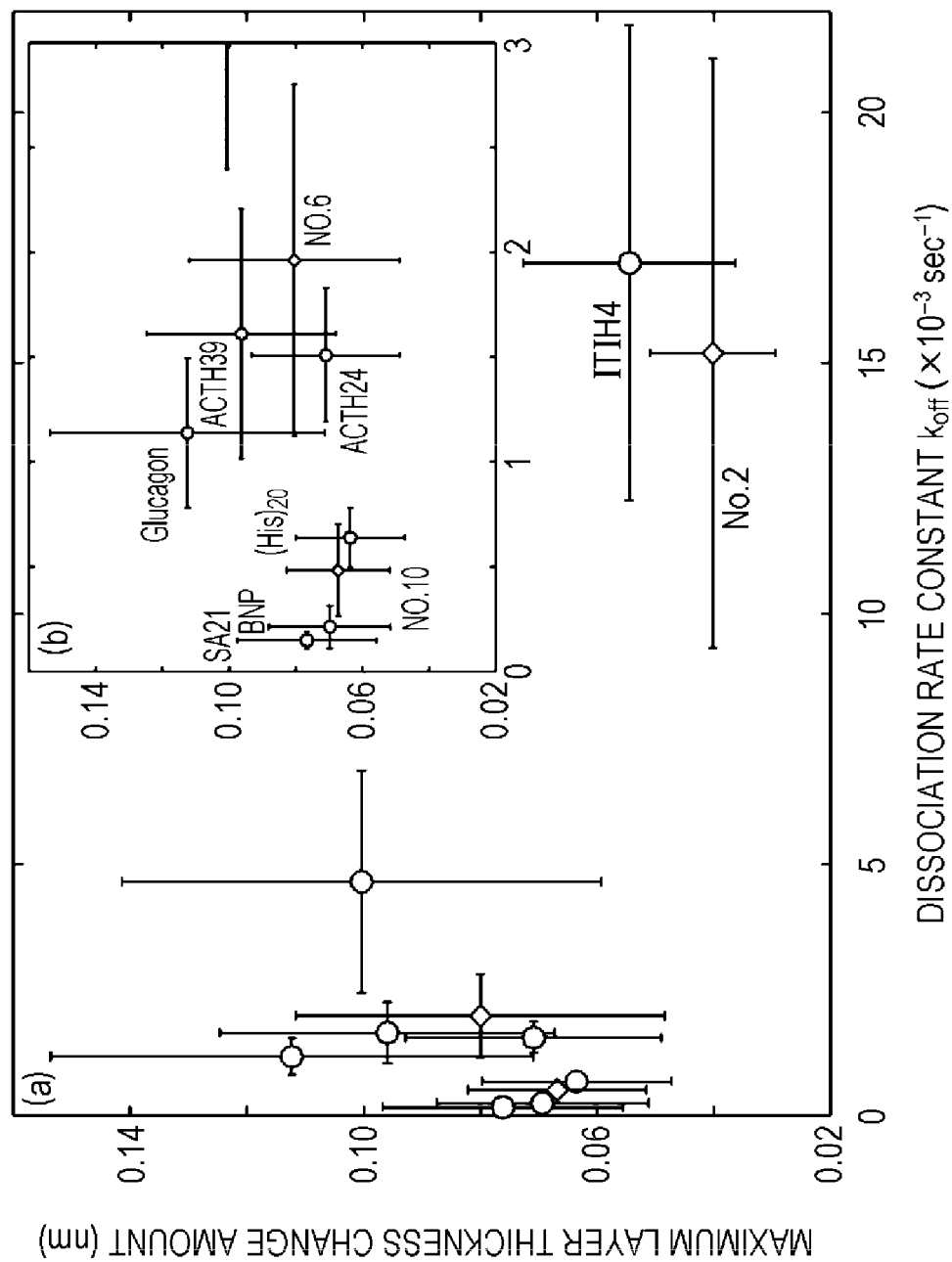

DEVICE, NON-TRANSITORY COMPUTER-READABLE STORAGE MEDIUM, AND METHOD FOR DETERMINING TYPE OF TARGET PEPTIDE

CROSS REFERENCE TO RELATED APPLICATIONS

This application claims priority from prior Japanese Patent Application No. 2014-154333, filed on Jul. 29, 2014, entitled "DEVICE, PROGRAM, AND METHOD FOR DETERMINING TYPE OF TARGET PEPTIDE", the entire contents of which are incorporated herein by reference.

TECHNICAL FIELD

The present invention relates to a device, a non-transitory computer-readable storage medium and a method for determining the type of target peptide.

BACKGROUND

A method for identifying a peptide includes, for example, a method for detecting a peptide by mass spectrometry (refer to US 2006/0243899 A).

The method described in US 2006/0243899 A is carried out as follows. First, a sample containing a specific substance to be measured such as a target peptide and a substance other than the specific substance is mixed with a matrix that is more likely to ionize the specific substance than the substance other than the specific substance. Then, the obtained mixture is irradiated with a laser beam, and the specific substance is specifically ionized. Thereafter, a mass spectrum of the ionized substance is obtained.

However, it is desired to more easily determine the type of the peptide.

SUMMARY OF THE INVENTION

The scope of the present invention is defined solely by the appended claims, and is not affected to any degree by the statements within this summary.

A first aspect of the present invention provides a device for determining a type of target peptide including: an acquisition unit that obtains first to third information on a target peptide contained in a test sample; a storage unit that stores first to third information on a known peptide obtained using a standard sample containing the known peptide; and a controller that compares the first to third information on the target peptide obtained from the test sample with the first to third information on the known peptide stored in the storage unit and determines whether or not the target peptide is the known peptide, wherein the first information is a dissociation rate constant when the target peptide dissociates from a protein, in a solid phase carrier in which the target peptide is immobilized on a support through the protein binding to a peptide, the second information is a maximum value of the layer thickness change amount on the support, and the third information is information indicating that the dissociation mode of a peptide and the protein is either a single dissociation mode or a multiple dissociation mode.

A second aspect of the present invention provides a non-transitory computer-readable storage medium storing a program that, when executed by a processor, causes the processor to execute operations comprising: obtaining first to third information on a target peptide contained in a test sample, reading out, from a memory, first to third information on a known peptide obtained using a standard sample containing the known peptide, and comparing the first to third information on the target peptide obtained from the test sample with the first to third information on the known peptide read out from the memory and determining whether or not the target peptide is the known peptide, wherein the first information is a dissociation rate constant when the target peptide dissociates from a protein, in a solid phase carrier in which the target peptide is immobilized on a support through the protein binding to a peptide, the second information is a maximum value of the layer thickness change amount on the support, and the third information is information indicating that the dissociation mode of a peptide and the protein is either a single dissociation mode or a multiple dissociation mode.

A third aspect of the present invention provides a method for determining a type of target peptide including: (a) preparing a solid phase carrier by contacting a protein immobilized carrier in which a protein binding to a peptide is immobilized on a support with a test sample containing the target peptide to form a complex of the target peptide and the protein on the support; (b) obtaining a maximum value of a layer thickness change amount on the support by measuring (i) changes in the layer thickness on the support of the protein immobilized carrier when the target peptide binds to the protein, (ii) changes in the layer thickness on the support of the solid phase carrier when the target peptide dissociates from the protein, or (iii) both of the changes; (c) obtaining a dissociation rate constant of the target peptide when the target peptide dissociates from the protein by measuring changes in the layer thickness on the support of the solid phase carrier; (d) determining that a dissociation mode of the target peptide and the protein is either a single dissociation mode or a multiple dissociation mode; (e) comparing the dissociation rate constant of the target peptide, the maximum value of the layer thickness change amount, and the dissociation mode with a dissociation rate constant, a maximum value of a layer thickness change amount, and a dissociation mode which are previously measured using a known peptide in a manner similar to the target peptide; and (f) determining whether or not the target peptide is the known peptide based on the comparison result in the step (e).

BRIEF DESCRIPTION OF THE DRAWINGS

FIG. 9 is an explanatory view illustrating determination results obtained in Comparative Example 1;

DETAILED DESCRIPTION OF THE PREFERRED EMBODIMENTS

1. Definition of Term

Figure 1:
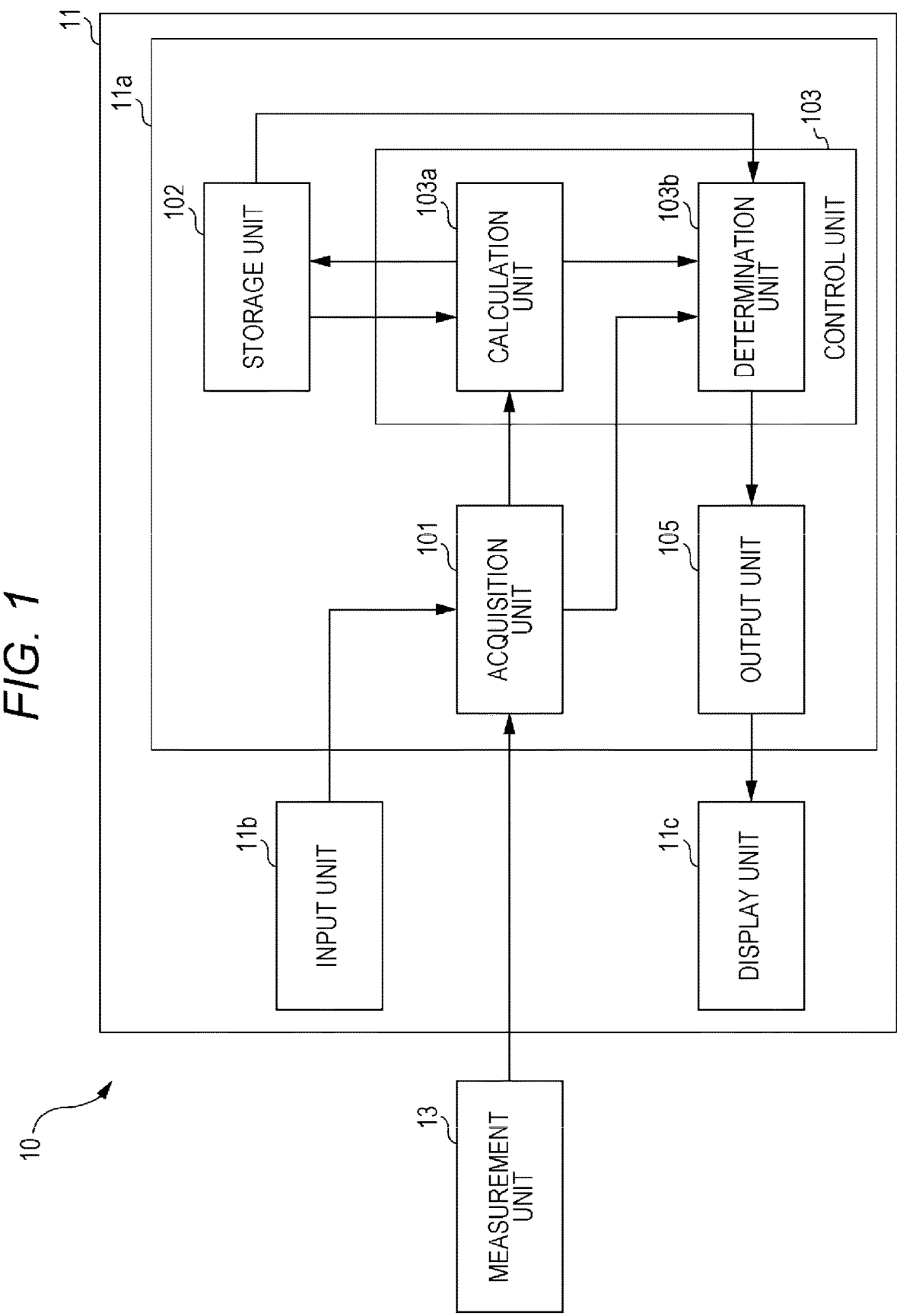
FIG. 1 is a functional block diagram of a device for determining a type of target peptide.

The term "X or more" used herein means that a value of X and a value larger than X are included. The term "Y or less" used herein means that a value of Y and a value smaller than Y are included. A numerical range such as "between X and Y" based on endpoints includes all the numbers included in the ranges, rational numbers, and the described endpoints.

The term "layer" used herein means a protein layer formed on the surface of a support. Usually, the protein layer is considered to be a membrane on the matrix surface. In the art, the thickness of the layer is referred to as "membrane thickness" or "layer thickness." The thickness of the layer is measured by an optical method such as reflection interference spectroscopy as described hereinbelow. In this case, the thickness of the layer is also called "optical thickness" or "optical depth."

Unless otherwise specified, the term "peptide" used herein includes a target peptide and a peptide other than the target peptide. Here, the term "peptide" means a compound containing between 2 and 129 amino acids bound through a peptide linkage. The term "protein" means a compound containing 130 or more of amino acids bound through a peptide linkage. Both the "peptide" and the "protein" used in the embodiment may be naturally derived substances or artificially synthesized substances.

2. Method for Determining Type of Target Peptide

The method for determining a type of target peptide according to the embodiment includes: (a) preparing a solid phase carrier by contacting a protein immobilized carrier in which a protein binding to a peptide is immobilized on a support with a test sample containing the target peptide to form a complex of the target peptide and the protein on the support; (b) obtaining a maximum value of a layer thickness change amount on the support by measuring changes in the layer thickness on the support of the protein immobilized carrier when the target peptide binds to the protein, changes in the layer thickness on the support of the solid phase carrier when the target peptide dissociates from the protein or both of the changes; (c) obtaining a dissociation rate constant of the target peptide when the target peptide dissociates from the protein by measuring changes in the layer thickness on the support of the solid phase carrier; (d) determining that the dissociation mode of the target peptide and the protein is either a single dissociation mode or a multiple dissociation mode; (e) comparing the dissociation rate constant of the target peptide, the maximum value of the layer thickness change amount, and the dissociation mode with the dissociation rate constant, the maximum value of the layer thickness change amount, and the dissociation mode which are previously measured using a known peptide in a manner similar to the target peptide; and (f) determining whether or not the target peptide is the known peptide based on the comparison result in the step (e) (hereinafter referred to as "method according to the embodiment").

In the method according to the embodiment, based on the fact that the peptide has inherent characteristics corresponding to the type of peptides, a type of target peptide is determined according to the following items (I) to (III): (I) a dissociation rate constant when a peptide dissociates from a protein in a solid phase carrier; (II) a maximum value in the layer thickness change amount on a support in binding and dissociation between the protein and the peptide; and (III) whether the dissociation mode of the peptide and the protein is either a single dissociation mode or a multiple dissociation mode.

In the method according to the embodiment, a solid phase carrier is prepared in the step (a). In the step (a), a test sample containing a target peptide is in contact with a protein immobilized on a support of a protein immobilized carrier to form a complex of the target peptide and the protein. Thus, a complex layer is formed on the support of the protein immobilized carrier.

The solid phase carrier includes a protein binding to a peptide, a support, and a target peptide. In the solid phase carrier, the target peptide is immobilized on the support through the protein.

The protein immobilized carrier includes a protein binding to a peptide and a support. In the protein immobilized carrier, the protein binding to the peptide is immobilized on the support, directly or indirectly through an adhesive. In the protein immobilized carrier, the protein may be immobilized on the whole surface of the support or may be immobilized on a part of the support surface at a level required to measure the layer thickness as described below. The protein is layered on the surface of the support.

The support may be a support capable of immobilizing the protein binding to the peptide. Therefore, in the case of directly immobilizing the protein on the support, examples of the support include a support made of a substance or a material to which the protein is attached or bound and a support obtained by modifying the surface of a substrate with a substance or a material to which the protein is attached or bound, but not particularly limited thereto. Examples of the substance or the material to which the protein is attached or bound include silicon nitride, ice, nickel, gold, amino acid compounds, polyether polymer compounds, carboxymethyl cellulose, ethylene glycol compounds, digoxigenin, vitamin derivatives, antibodies, and avidin, but not particularly limited thereto. Examples of the material of the support include silicon compounds such as silica, silicon, and quartz, silicone resins, polystyrene, acrylic resins, quartz, aluminum, gold, and carbon, but not particularly limited thereto. The modification of the surface of the substrate with the material to which the protein is attached or bound may be performed by, for example, a chemical vapor deposition method. On the other hand, in the case of indirectly immobilizing the protein on the support through an adhesive, examples of the material of the support include materials similar to the materials of the substrate, but not particularly limited thereto. The adhesive include, for example, a molecular adhesive (product name: Cell-Tack, manufactured by BD biosciences), but not particularly limited thereto. The shape of the support may have a surface capable of immobilizing the protein. Examples of the shape of the support include a sheet shape and a particulate shape, but not particularly limited thereto. The size of the support may be a size suitable for measuring the first, second, and third information.

Specific examples of the support include a silicon nitride substrate, a nickel bead, a gold particle, a coacervate, an amino acid compound-modified substrate, a polyether polymer compound membrane, a carboxymethyl cellulose substrate, an ethylene glycol self-assembled monolayer, a digoxigenin-immobilized substrate, a vitamin derivative-immobilized bead, a Langmuir-Blodgett membrane, an antibody-immobilized substrate, and an avidin-immobilized bead, but not particularly limited thereto.

Examples of the protein binding to the peptide include proteins present in body fluid such as blood, enzymes, receptors, major histocompatibility complexes, biomembrane transporters, and aptamers containing the protein binding to the peptide, but not particularly limited thereto. Among them, proteins present in body fluid such as blood are preferred, and proteins present in blood are more preferred. Specific examples of the protein binding to the peptide include albumin, transthyretin, and globulin, but not particularly limited thereto. The binding mode of a peptide and a protein binding to the peptide includes a hydrogen bond, a van der Waals force bond, a hydrophobic bond, an ionic bond, and a coordinate bond, however, it is not particularly limited thereto.

The amount of the protein binding to the peptide to be immobilized on per a surface area of 1 $mm^2$ of a support can be appropriately determined depending on the application of the method according to the embodiment, the type of the protein and the like. Usually, the amount of the protein binding to the peptide to be immobilized on per a surface area of 1 $mm^2$ of a support is preferably from 0.02 ng to 2 ng, from the viewpoint of favorably measuring changes in the layer thickness on the support in the step (b) as described hereinbelow. The amount of the protein binding to the peptide to be immobilized on per a surface area of 1 $mm^2$ of a support is more preferably 0.05 ng or more, still more preferably 0.1 ng or more, still more preferably 1 ng or less, still more preferably 0.5 ng or less from the viewpoint of ensuring the convenience of measurement.

When the protein binding to the peptide is directly immobilized on a support, immobilization of the protein to the support can be performed by contacting a protein-containing solution with a support, applying a protein-containing solution to the surface of a support, immersing a support in a protein-containing solution, or pouring a protein-containing solution onto the surface of a support or the like. When the protein binding to the peptide is indirectly immobilized on a support through an adhesive, immobilization of the protein to the support can be performed by adhering an adhesive to the surface of a support and then attaching the protein onto the adhesive on the support, adhering an adhesive to the protein and then attaching the protein onto the surface of a support through the adhesive or the like.

Examples of the test sample include samples which may contain target peptides; body fluids such as blood and saliva; samples derived from living body such as urine (biological samples); peptide pharmaceutical preparations; peptide-containing cosmetic preparations; peptide-containing foods; peptide-containing adhesives for industrial use; peptide-containing fillers for column chromatography; and peptide-containing biomass fuels, but not particularly limited thereto. The target peptide may be a naturally occurring peptide or a synthetic peptide. Examples of the target peptide include oligopeptide; polypeptide; and peptide compounds such as a cyclic peptide and a peptide mimic, but not particularly limited thereto. The target peptide may be a peptide used medicinally or a peptide compound. The test sample may contain a solvent for dissolving the target peptide. Examples of the solvent include buffers such as a phosphate buffer, purified water, physiological saline, and phosphate buffered saline, but not particularly limited thereto. When the test sample contains an aqueous solvent (e.g., purified water or a buffer), the pH of the test sample is preferably a pH that maintains the physiological function of the target peptide. If necessary, the test sample may contain a stabilizer for the target peptide.

The protein immobilized carrier can be contacted with the test sample using, for example, a measurement device used to measure changes in the layer thickness. The contact of the protein immobilized carrier and the test sample can be performed by supplying a test sample-containing liquid onto the surface on which a protein in a protein immobilized carrier is immobilized at a constant flow rate, dropping a test sample-containing liquid onto the surface on which a protein in a protein immobilized carrier is immobilized, immersing a protein immobilized carrier in a test sample-containing liquid, spin-coating the surface on which a protein in a protein immobilized carrier is immobilized with a test sample-containing liquid, or another method such as electric field adsorption, electroosmosis, ionization spraying or tableting. The amount of the test sample to be contacted with the protein immobilized carrier can be appropriately determined depending on the type of test samples. The temperature when contacting the protein immobilized carrier with the test sample can be appropriately determined in the temperature range in which the protein binding to the peptide is bound to the target peptide, depending on the type of target peptides, the type of proteins binding to peptides, and the use of the method according to the embodiment. The time required to contact the protein immobilized carrier with the test sample can be appropriately determined depending on the type of target peptides, the type of proteins binding to peptides, and the use of the method according to the embodiment.

In the step (b) of the method according to the embodiment, a maximum value of the layer thickness change amount on the support is obtained by measuring changes in the layer thickness on the support of the protein immobilized carrier when the target peptide binds to the protein of the protein immobilized carrier and the change of the layer thickness on the support of the solid phase carrier when the target peptide dissociates from the protein in the solid phase carrier. As a result of the step (b), the maximum value of the layer thickness change amount can be obtained as the second information as described hereinbelow.

The maximum value of the layer thickness change amount is a value when a difference between the layer thickness on the support of the protein immobilized carrier (layer thickness before the peptide binds to the protein) and the layer thickness on the support of the solid phase carrier (layer thickness after the peptide binds to the protein) becomes maximum. The maximum value of the layer thickness change amount is a difference between the optical thickness of the protein layer on the support when only the protein is substantially immobilized on the support and the optical thickness of the complex layer on the support when the complex of the peptide and the protein is formed on the support. The optical thickness of the protein layer may be the optical thickness before the peptide is contacted with the protein or may be the optical thickness after the peptide is contacted with the protein and the peptide is substantially dissociated. The concept of "the maximum value of the layer thickness change amount" used herein encompasses both a maximum value of the layer thickness change amount when the target peptide binds to the protein of the protein immobilized carrier and a maximum value of the layer thickness change amount when the target peptide dissociates from the protein in the solid phase carrier.

For example, the reflection interference spectroscopy may be used to measure changes in the layer thickness. In the method according to the embodiment, the reflection interference spectroscopy is preferred from the viewpoint of easily measuring changes in the layer thickness.

The reflection interference spectroscopy is the spectroscopy based on white light interference in the layer. When the layer thickness changes, white light interference occurs in the reflected light with which the layer is irradiated due to phase shifting. At this time, a bottom wavelength of a spectral reflectance curve of the reflected light is shifted by the white light interference. In the method of the embodiment, a wavelength variation $\Delta\lambda$ of the bottom wavelength of the spectral reflectivity curve of the reflected light is successively measured as an index of changes in the layer thickness so that the layer thickness change amount on the support can be measured. In measurement of the wavelength variation $\Delta\lambda$ a device for measuring layer thickness displacement and intermolecular interaction [product name: MI-Affinity (registered trademark), manufactured by Konica Minolta, Inc.] or the like may be used. As used herein, the wavelength variation $\Delta\lambda$ encompasses a wavelength variation when the target peptide binds to the protein, a wavelength variation when the target peptide dissociates from the protein, and both of the wavelength variations. The measurement of the wavelength variation $\Delta\lambda$ is performed during the contact of the test sample with the protein immobilized carrier in the step (a) (for example, from the start of the contact to the end of the contact), after the end of the contact of the test sample with the protein immobilized carrier in the step (a) or both during the contact and after the end of the contact. In the step (a), when the wavelength variation $\Delta\lambda$ is measured during the contact of the test sample with the protein immobilized carrier, the temperature and time required to measure the wavelength variation $\Delta\lambda$ are similar to the temperature and contact time during the contact of the test sample with the protein immobilized carrier. In the step (a), when the wavelength variation $\Delta\lambda$ is measured after the end of the contact of the test sample with the protein immobilized carrier, the temperature and time required to measure the wavelength variation $\Delta\lambda$ can be appropriately determined depending on the type of target peptides, the type of proteins binding to peptides, and the use of the method according to the embodiment.

When a target peptide binds to a protein, the measurement of the wavelength variation $\Delta\lambda$ can be performed by the following procedure using the device for measuring layer thickness displacement and intermolecular interaction [product name: MI-Affinity (registered trademark), manufactured by Konica Minolta, Inc.]. First, a support and a flow cell are mounted on the device for measuring layer thickness displacement and intermolecular interaction. Next, a running buffer is injected into a flow path formed between the support and the flow cell so as to equilibrate the surface of the support. After that, a solution containing a protein binding to a peptide is injected into the flow path at a constant flow rate and the protein is attached onto the surface of the support. Accordingly, a protein immobilized carrier having the protein immobilized on the support can be obtained. At a time when a predetermined time has elapsed since the attachment of the protein to the surface of the support, a test sample is injected into the flow path at a constant flow rate. In injecting a protein-containing solution or a test sample into the flow path, the wavelength variation $\Delta\lambda$ of the bottom wavelength of the spectral reflectivity curve of the reflected light when the flow path is irradiated with white light is measured with time. Accordingly, a sensorgram showing the time-dependent change of the wavelength variation $\Delta\lambda$ can be obtained. The measurement of changes in the layer thickness need not be started from the time of production of the protein immobilized carrier, and may be started, for example, from the time of contact of the test sample with the previously prepared protein immobilized carrier.

When a target peptide dissociates from a protein, the measurement of the wavelength variation $\Delta\lambda$ can be performed by the following procedure using the device for measuring layer thickness displacement and intermolecular interaction [product name: MI-Affinity (registered trademark), manufactured by Konica Minolta, Inc.]. First, a support and a flow cell are mounted on the device for measuring layer thickness displacement and intermolecular interaction. Next, a running buffer is injected into a flow path formed between the support and the flow cell so as to equilibrate the surface of the support. After that, a solution containing a protein binding to a peptide is injected into the flow path at a constant flow rate and the protein is attached onto the surface of the support. Accordingly, a protein immobilized carrier having the protein immobilized on the support can be obtained. At a time when a predetermined time has elapsed since the attachment of the protein to the surface of the support, a test sample is injected into the flow path at a constant flow rate. After injection of the test sample and after binding of the peptide to the protein, the wavelength variation $\Delta\lambda$ of the bottom wavelength of the spectral reflectivity curve of the reflected light when the flow path is irradiated with white light is measured with time. Accordingly, a sensorgram showing the time-dependent change of the wavelength variation $\Delta\lambda$ can be obtained.

In the step (c) of the method according to the embodiment, the dissociation rate constant of a target peptide when the target peptide dissociates from the protein is obtained by measuring changes in the layer thickness on the support of the solid phase carrier. As a result of the step (c), the dissociation rate constant as the first information described hereinbelow can be obtained.

The dissociation rate constant can be calculated based on, for example, the time-dependent change of the layer thickness change amount during the period from the time when the wavelength variation (i.e., the layer thickness change amount on the support) after the contact of the peptide and the protein immobilized carrier becomes a maximum value to the time when the wavelength variation becomes a minimum value, but the method is not particularly limited thereto. The dissociation rate constant can be calculated by, for example, the following procedure. A sensorgram showing the time-dependent change of the layer thickness change amount (wavelength variation $\Delta\lambda$) during the period from the start to the end of the dissociation of the peptide is first created. Then, the obtained sensorgram is subjected to least-square-based curve fitting using software for statistical analysis and graph generation [HULINKS Inc., product name: Kaleida Graph] to obtain an approximate curve of the sensorgram. The equation representing the obtained approximate curve is compared with the equation represented by Equation (I):

[Equation 1]

$$\Delta \lambda = a \times e^{-k_1 \cdot t} + b \times e^{-k_2 \cdot t} \quad (I)$$

(wherein, $\Delta\lambda$ represents a layer thickness change amount, a, b, $k_1$, and $k_2$ represent arbitrary numbers determined by curve fitting, and t represents elapsed time). When the a value in Equation (I) is higher than the b value (a>b), the $k_1$ value can be obtained as the dissociation rate constant $k_{off}$ of the peptide.

When the a value is lower than the b value (a<b), the $k_2$ value can be obtained as the dissociation rate constant $k_{off}$ of the peptide.

Subsequently, the step (d) of the method according to the embodiment determines that the dissociation mode of a peptide and a protein is either a single dissociation mode or a multiple dissociation mode. As a result of the step (d), the third information as described hereinbelow is obtained.

In the method according to the embodiment, the dissociation mode of a peptide and a protein binding to the peptide is classified into a single dissociation mode and a multiple dissociation mode depending on the type of peptides. The term "single dissociation mode" used herein means a mode in which dissociation between the peptide and the protein at approximately one type of dissociation rate is observed. The term "multiple dissociation mode" used herein means a mode in which dissociation between the peptide and the protein at multiple types of dissociation rates is observed. The difference between the dissociation modes is considered due to the tertiary structures of the peptide and the protein, the shape of binding site in the protein, the number of binding sites, and the affinity between the peptide and the protein.

In the step (d), the dissociation mode can be determined based on the coefficient of the equation representing an approximate curve that is found by the least square method from the sensorgram after the time when the layer thickness change amount has the maximum value. The equation representing an approximate curve includes, for example, Equation (I).

When the dissociation mode is classified using Equation (I), the dissociation mode can be classified using the b value of Equation (I) based on the following determination criteria.

<Determination Criteria on Classification of Dissociation Mode>

When the b value in Equation (I) is lower than a predetermined threshold for classifying the dissociation mode into a single dissociation mode and a multiple dissociation mode, the dissociation mode of the peptide from the protein is determined to be the single dissociation mode. When the b value in Equation (I) is the threshold or more, the dissociation mode of the peptide from the protein is determined to be the multiple dissociation mode.

The threshold is from 0.109 to 0.519 from the viewpoint of reducing the influence of variations in determination results when using different test samples. The threshold is more preferably from 0.163 to 0.319 from the viewpoint of ensuring the reproducibility of measurement when using the same test sample.

Subsequently, in the step (e) of the method according to the embodiment, the dissociation rate constant of the target peptide, the maximum value of the layer thickness change amount, and the dissociation mode are compared with the dissociation rate constant which has been previously obtained by measuring the known peptide in a manner similar to that of the target peptide, the maximum value of the layer thickness change amount, and the dissociation mode. In the step (e), the first to third information on a target peptide is compared with the first to third information on a known peptide.

In the step (e), the known peptide to be compared may be one type or multiple types (two or more types). For example, the first to third information on the target peptide is compared with the first to third information on a first type of known peptide, and then the first to third information on the target peptide is compared with the first to third information on a second type of known peptide. The upper limit of the type of the known peptide to be compared can be appropriately determined depending on the application of the method according to the embodiment.

The comparison of the first information evaluates whether the dissociation rate constant of the target peptide is equal or similar to the dissociation rate constant of a specific known peptide. The term "similar to the dissociation rate constant of a specific known peptide" means, for example, to satisfy at least one of the following conditions:

the value calculated by Equation (II) is 0.315 or less, preferably 0.129 or less:

([value of dissociation rate constant of specific known peptide]−[value of dissociation rate constant of target peptide])/[value of dissociation rate constant of specific known peptide]      (II); and the condition represented by Equation (III) is satisfied:

$$(AVE-SD) < M < (AVE+SD) \quad (III)$$

(wherein, AVE represents an average of the dissociation rate constants obtained by repeatedly measuring the known peptide, SD represents a value of standard deviation, and M represents a dissociation rate constant of the target peptide to be determined whether or not it is similar).

"AVE−SD" and "AVE+SD" each independently represents a dissociation rate constant of a known peptide. The dissociation rate constant of the known peptide is a value specific to known peptides to be referred.

The comparison of the second information evaluates whether the maximum value of the layer thickness change amount when the target peptide is used is equal or similar to the maximum value of the layer thickness change amount when the specific known peptide is used. The term "similar to the maximum value of the layer thickness change amount when the specific known peptide is used" means, for example, to satisfy at least one of the following conditions:

the value obtained by Equation (IV) is 0.249 or less, preferably 0.112 or less:

([maximum value of amount of change in layer thickness when specific known peptide is used]−[maximum value of amount of change in layer thickness when target peptide is used])/[maximum value of amount of change in layer thickness when specific known peptide is used]      (IV); and the condition represented by Equation (V) is satisfied:

$$(ave-sd) < m < (ave+sd) \quad (V)$$

(wherein, ave represents an average of the maximum values of the layer thickness change amount which has been obtained by repeatedly measuring the known peptide, sd represents a value of standard deviation, and m represents a maximum value of the layer thickness change amount when using the target peptide to be determined whether or not it is similar).

The comparison of the third information evaluates whether the dissociation mode of the target peptide and the protein is equal to the dissociation mode of the specific known peptide and the protein (the single dissociation mode or the multiple dissociation mode).

In the step (f) of the method according to the embodiment, the step (e) determines whether or not the target peptide is the known peptide based on the comparison result. In the step (f), the determination device as described hereinbelow can be used.

When the dissociation rate constant of one type of known peptide, the maximum value of the layer thickness change amount, and the dissociation mode are used in the step (e), the step (f) determines whether or not the target peptide corresponds to the known peptide based on the comparison result obtained in the step (e). On the other hand, when the dissociation rate constant, the maximum value of the layer thickness change amount, and the dissociation mode regarding each of the multiple types of known peptides are used in the step (e), the step (f) determines whether or not the target peptide corresponds to any of the multiple types of known peptides based on the comparison result obtained in the step (e).

In the step (f), when the dissociation rate constant of the target peptide and the maximum value of the layer thickness change amount are equal or similar to the dissociation rate constant of the specific known peptide and the maximum value of the layer thickness change amount and the dissociation mode of the target peptide is equal to the dissociation mode of the specific known peptide, it is possible to determine that the target peptide is highly likely to be the specific known peptide. On the other hand, when the dissociation rate constant of the target peptide and the maximum value of the layer thickness change amount are neither equal nor similar to the dissociation rate constant of the specific known peptide and the maximum value of the layer thickness change amount and the dissociation mode of the target peptide is different from the dissociation mode of the specific known peptide, it is possible to determine that the target peptide is highly likely not to be the specific known peptide.

In the method according to the embodiment, a graph obtained by plotting the first to third information on a known peptide (hereinafter also referred to as "peptide map") may be used to determine the type of target peptides. The use of the peptide map in the method according to the embodiment enables to determine visually and easily whether or not the target peptide is the specific known peptide. Examples of the peptide map include a peptide map including a first map in which the first information on the known peptide in the single dissociation mode is defined as an X-axis and the second information is defined as a Y-axis and a second map in which the first information on the known peptide in the multiple dissociation mode is defined as an X-axis and the second information is defined as a Y-axis; and a peptide map including a first map in which the second information on the known peptide in the single dissociation mode is defined as an X-axis and the first information is defined as a Y-axis and a second map in which the second information on the known peptide in the multiple dissociation mode is defined as an X-axis and the first information is defined as a Y-axis, but not particularly limited thereto.

In the step (f), when the type of target peptides is determined using the peptide map, the indexes to be used are, for example, a distance between a coordinate point representing a target peptide and a coordinate point representing a specific known peptide and a size of the area of a portion where a predetermined range for using the coordinate point representing a target peptide as the central point is overlapped with a predetermined range for using the coordinate point representing a specific known peptide as the central point. When the distance between the coordinate points is used as an index, the target peptide can be determined as the known peptide located at the coordinate point closest to the coordinate point of the target peptide. When the area of the overlapped portion is used as an index, the target peptide can be determined as the known peptide having the largest overlapped area.

3. Determination Device and Program

Subsequently, the determination device to be used for the method for determining a type of target peptide will be described in more details with reference to the attached drawings, however the present invention is not limited only to the embodiment.

A determination device 10 illustrated in FIG. 1 includes a computer system 11 and a measurement unit 13 connected to the computer system 11. The computer system 11 includes a computer main body 11a, an input unit 11b, and a display unit 11c.

The computer main body 11a includes an acquisition unit 101 that is a receiving means for obtaining first to third information from the input unit 11b and the measurement unit 13, a storage unit 102 that is a storage means for storing first to third information, a control unit 103 that is a control means for determining whether or not a target peptide is a known peptide, and an output unit 105 that displays the determination result on the display unit 11c. The acquisition unit 101 sends first to third information obtained from the input unit 11b and the measurement unit 13 to the control unit 103. The storage unit 102 stores first to third information on both a target peptide and a known peptide and criteria for determining the target peptide. The control unit 103 sends the first to third information obtained from the acquisition unit 101 to the storage unit 102. The control unit 103, comprising a calculation unit 103a and a determination unit 103b, determines the type of the target peptide based on the first to third information on both the target peptide and the known peptide stored in the storage unit 102 according to the criteria for determining the type of target peptide stored in the storage unit 102. The control unit 103, based on the determination result, generates screen information including graphs showing first to third information on a target peptide and first to third information on multiple types of known peptides and the determination result of the target peptide. The output unit 105 outputs the graphs showing first to third information on a target peptide and first to third information on multiple types of known peptides and the determination result of the target peptide to the display unit 11c. The display unit 11c displays the graphs and the determination result. When a printer is connected to the output unit 105, the output unit 105 allows the printer to print the determination result.

The storage unit 102 may store the first to third information on multiple types of known peptides. In this case, the control unit 103 compares the first to third information on a target peptide with the first to third information on multiple types of known peptides and determines whether or not the target peptide is any one of the multiple types of known peptides based on the obtained comparison result.

In the embodiment, the measurement unit 13 is a device that measures first to third information on a target peptide contained in a test sample by detecting the white light interference.

Figure 2:
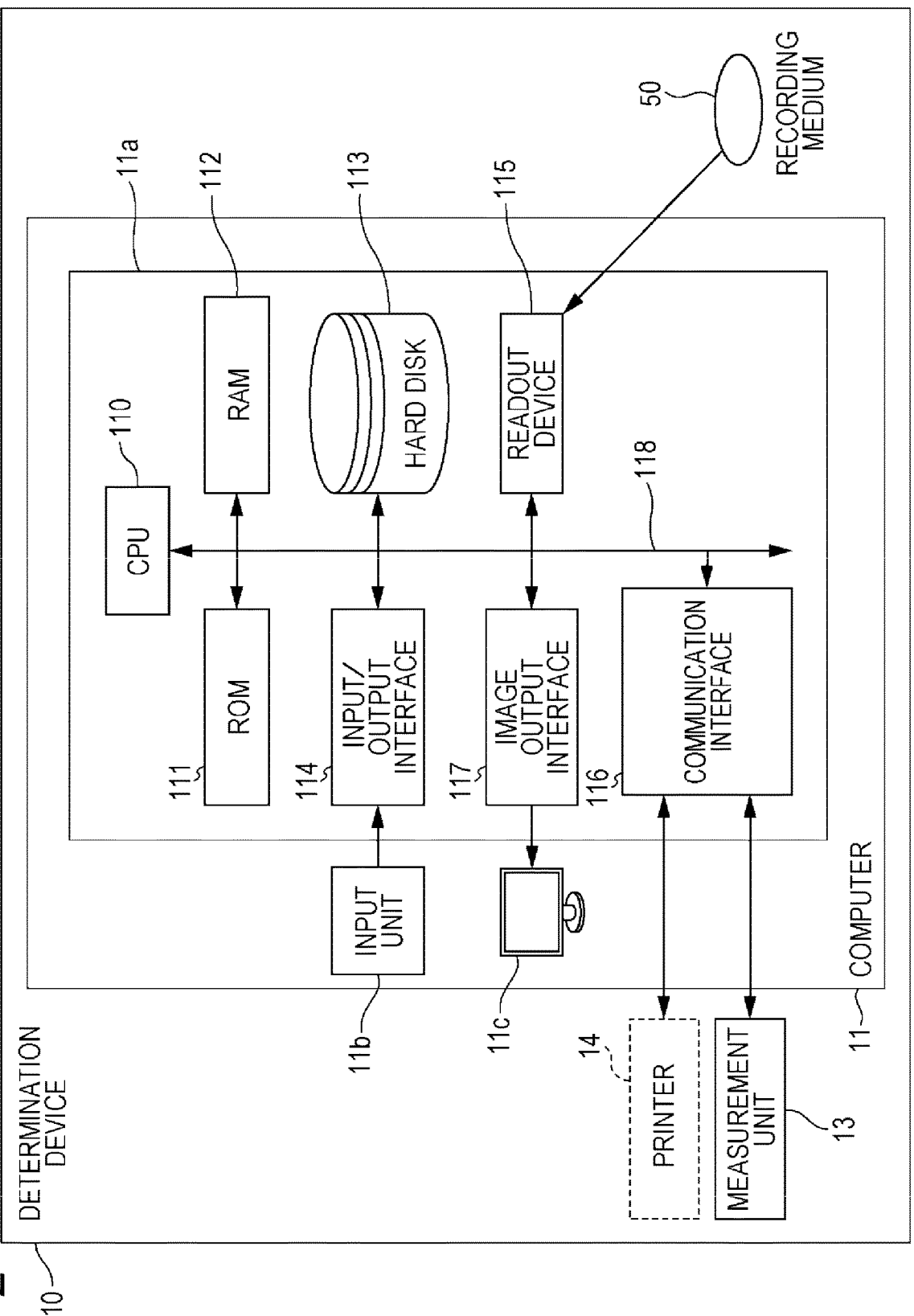
FIG. 2 is a hardware configuration diagram of the determination device illustrated in FIG. 1.

Subsequently, the hardware configuration of the determination device in FIG. 1 will be described. The computer main body 11a shown in FIG. 2 includes a CPU (Central Processing Unit) 110, ROM (Read Only Memory) 111, RAM (Random Access Memory) 112, a hard disk 113, an input/output interface 114, a readout device 115, a communication interface 116, and an image output interface 117. The CPU 110, ROM 111, RAM 112, the hard disk 113, the input/output Interface 114, the readout device 115, the communication interface 116, and the image output interface 117 are data-communicably connected via a bus 118.

When the CPU 110 executes the application program, the computer functions as each of the functional blocks described above. Accordingly, the computer system serves as a terminal that is a terminal as a device for determining a type of target peptide. An operating system to be executed by the CPU 110, computer programs such as application programs (the computer program for determining a type of target peptide), and data for executing the computer programs are installed on the hard disk 113. The readout device 115 can read out data such as the computer program or first to third information on known peptides stored on a portable recording medium 50. The input/output Interface 114 is connected to the input device 11b such as a keyboard and a mouse. A user can input data into the computer main body 11a by means of the input unit 11b. The communication interface 116 is, for example, an Ethernet (registered trademark) interface. The computer system 11 can send printing data to a printer 14 via the communication interface 116. The image output interface 117 is connected to the display unit 11c including a LCD, a CRT and the like. Accordingly, the display unit 11c can input an image signal according to image data such as the determination result provided by the CPU 110.

Figure 3:
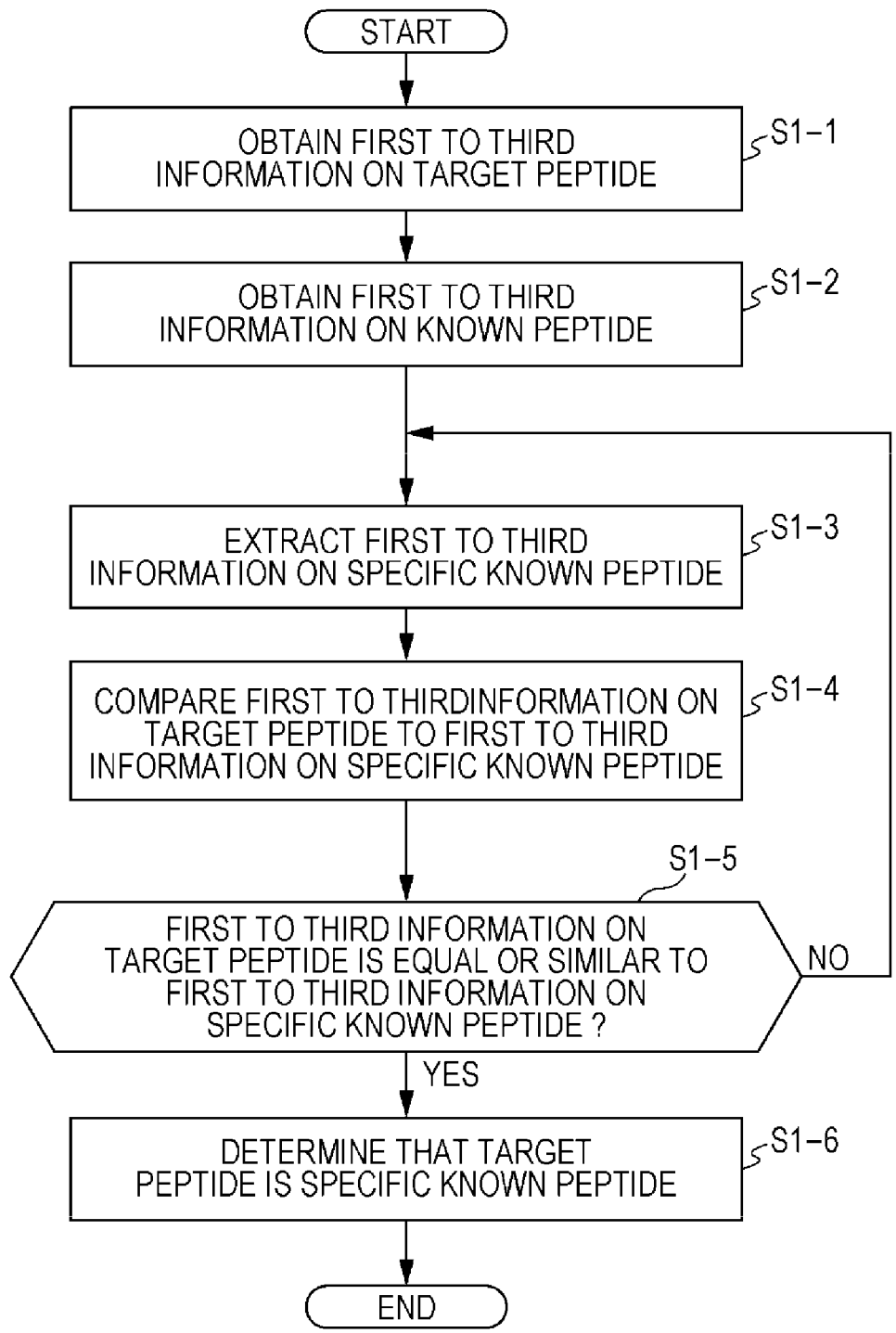
FIG. 3 is a flow chart of an example of determining a type of target peptide.

Subsequently, the procedure for determining the type of the target peptide carried out by the determination device 10 will be described. FIG. 3 is a flow chart for determining the type of the target peptide using the determination device 10 illustrated in FIG. 1. In FIG. 3, an example is illustrated in which multiple types of known peptides are used. However, in determination of the type of the target peptide based on the determination device 10 according to the embodiment, one type of known peptide may be used instead of using multiple types of known peptides.

In the step S1-1, the acquisition unit 101 of the determination device 10 obtains the first to third information on a target peptide from the measurement unit 13. In the step S1-1, if necessary, the control unit 103 may send the obtained first to third information on a target peptide to the storage unit 102. In the step S1-2, the control unit 103 reads out the first to third information on known peptides stored in the storage unit 102. In the step S1-3, the control unit 103 extracts first to third information on a specific known peptide from the obtained first to third information on known peptides. In the step S1-4, the control unit 103 compares the obtained first to third information on a target peptide with the first to third information on a specific known peptide extracted in the step S1-3. In the step S1-5, the control unit 103 determines whether or not the first to third information on a target peptide is equal or similar to the first to third information on a specific known peptide. In the step S1-5, when the control unit 103 determines that the first to third information on a target peptide is equal or similar to the first to third information on a specific known peptide, the control unit 103 proceeds to the step S1-6. In the step S1-6, the control unit 103 determines that the target peptide is the specific known peptide and outputs data of the determination result to the output unit 105. Then, the step is ended. In the step S1-5, when the control unit 103 determines that the first to third information on a target peptide is not equal or similar to the first to third information on a specific known peptide, the control unit 103 returns to the step S1-3. The control unit 103 extracts first to third information on a specific known peptide again and executes the steps S1-4 to S1-6.

EXAMPLES

Hereinafter, the present invention will be described in detail with reference to Examples, however, the present invention is not limited thereto.

Example 1

(1) Preparation of Human Serum Albumin Solution

In Example 1, human serum albumin (hereinafter referred to as "HSA", manufactured by Sigma-Aldrich Co. LLC.) was used as a protein binding to a peptide. HSA powder was dissolved in purified desalting water to prepare an HSA solution. The HSA solution obtained was diluted with 0.1 M sodium phosphate buffer (pH 6.9) so as to have a concentration of HSA of 0.2 μM and an HSA solution was prepared.

(2) Production of HSA Sensor Chip

A substrate as a support [product name: sensor chip (unmodified) for MI-Affinity (registered trademark), model name: LCF-01, manufactured by Konica Minolta, Inc.] and a flow cell [product name: MI-Affinity (registered trademark) flow cell, model name: LCF-01, manufactured by Konica Minolta, Inc.] were mounted on a device for measuring intermolecular interaction [Konica Minolta, Inc., product name: MI-Affinity (registered trademark)]. The substrate is a substrate in which a silicon nitride thin layer is formed on the surface of a silicon wafer.

Then, a running buffer (0.1 M sodium phosphate buffer (pH 6.9)) was injected into a flow path formed between the substrate and the flow cell at a flow rate of 100 μL/min for 30 minutes or more so as to equilibrate the surface of the substrate. Thereafter, 100 μL of the HSA solution obtained in Example 1 (1) was injected into the flow path at a flow rate of 100 μL/min so as to attach HSA to the surface of the substrate. In injecting the running buffer or the sample, a liquid feeding pump for high-performance liquid chromatograph [product name: Prominence UFLC, manufactured by Shimadzu Corporation] and an autosampler [product name: Chromaster, manufactured by Hitachi, Ltd.] were used. As a result, a solid phase carrier having HSA immobilized on the surface thereon (hereinafter also referred to as "HSA sensor chip") was obtained. In injecting the HSA solution into the flow path, the wavelength variation Δλ of bottom wavelength of the spectral reflectivity curve of the reflected light when the flow path was irradiated with white light was measured with time, whereby a sensorgram showing the time-dependent change of the wavelength variation Δλ was obtained.

As a result, the obtained sensorgram exhibited a constant wavelength variation Δλ immediately after the injection of the HSA solution into the flow path. The wavelength variation Δλ is related to the fact that the wavelength interference of reflected light occurs with changes in the layer thickness. Thus, the wavelength variation Δλ reflects the layer thickness change amount of the solid phase carrier (hereinafter also referred to as "layer thickness change amount Δλ"). It is considered that the layer thickness is changed by the attachment of HSA to the surface of the substrate. Therefore, it is found that the obtained sensorgram exhibited a constant layer thickness change amount Δλ immediately after the injection of the HSA solution into the flow path.

Subsequently, the dissociation rate constant $k_{off}$ of HSA dissociating from the substrate was calculated from the sensorgram. The dissociation of HSA from the substrate is hardly observed in the sensorgram. Accordingly, the dissociation rate constant $k_{off}$ was not able to be calculated by curve fitting. However, the sensorgram shows that HSA was immobilized on the surface of the substrate for 28 hours or more. This suggests that the HSA sensor chip has high storage stability and high practicability.

The half-life [the time required for the amount of HSA attached on the surface of the substrate to decrease to one-half of the original amount] was obtained by dividing a natural logarithm (ln 2) by the dissociation rate constant $k_{off}$ of HSA. The results show that HSA was immobilized on the surface of the substrate for 7 hours or more. This suggests that the HSA sensor chip has high storage stability and high practicability.

(3) Preparation of Peptide Solution

A powder of adrenocorticotropic hormone (hereinafter also referred to as "ACTH") ACTH partial peptide at the 1-24 positions (hereinafter also referred to as "ACTH24"), ACTH partial peptide at the 1-39 positions (hereinafter also referred to as "ACTH39"), ACTH partial peptide at the 1-41 positions (hereinafter also referred to as "ACTH41"), albumin-binding peptide SA21, inter-α-trypsin inhibitor heavy chain 4 (hereinafter also referred to as "ITIH4"), glucagon, brain natriuretic peptide (hereinafter also referred to as "BNP"), fibrinogen α, arginine decapeptide [hereinafter also referred to as "(Arg)10"] or histidine eicosa peptide [hereinafter also referred to as "(His)20"] [manufactured by Biologica Co, Ltd.] was dissolved in purified desalting water to prepare a peptide solution. Then, the obtained peptide solution was diluted with 0.1 M sodium phosphate buffer so as to have a concentration of peptide of 2 μM and a peptide solution was prepared. The information of each of the peptides is shown in Table 1.

TABLE 1

| Known peptide | Amino acid sequence | SEQ ID NO: | The number of amino acid residues | Isoelectric point pI |
|---|---|---|---|---|
| ACTH24 | SYSMEHFRWGKPVGKKRRPVKVYP | 1 | 24 | 10.6 |
| ACTH39 | SYSMEHFRWGKPVGKKRRPVKVYPNAGENESAEAFPLEF | 2 | 39 | 9.3 |
| ACTH41 | GPSYSMEHFRWGKPVGKKRRPVKVYPNGAEDESAEAFPLEF | 3 | 41 | 8.3 |
| SA21 | RLIEDICLPRWGCLWEDD | 4 | 18 | 4.1 |
| ITIH4 | GESRNRNVHSGSTFFKYYLQGAKIPKPEASFS | 5 | 32 | 9.8 |
| Glucagon | HSQGTFTSDYSKYLDSRRAQDFVQWLMNT | 6 | 29 | 6.8 |
| BNP | SPKMVQGSGCFGRKMDRISSSSGLGCKVLRRH | 7 | 32 | 11 |
| Fibrinogen α | DEAGSEADHEGTHSTKRGHAKSRPV | 8 | 25 | 6.3 |
| (Arg) 10 | RRRRRRRRRR | 9 | 10 | 13 |
| (His) 20 | HHHHHHHHHHHHHHHHHHHH | 10 | 20 | 7.6 |
| ACTH15 | YSMEHFRWGKPVGKK | 11 | 15 | 10 |
| AB40 | DAEFRHDSGYEVHHQKLVFFAEDVGSNKGAIIGLMVGGVV | 12 | 40 | 5.3 |
| AB42 | DAEFRHDSGYEVHHQGKLVFFAEDVGSNKGAIIGLMVGGVVIA | 13 | 42 | 5.3 |
| Dynorphin A | YGGFLRRIRPKLK | 14 | 13 | 11.7 |
| Kininogen | HNLGHGHKHERDQGHGHQR | 15 | 19 | 8.8 |

Figure 4:
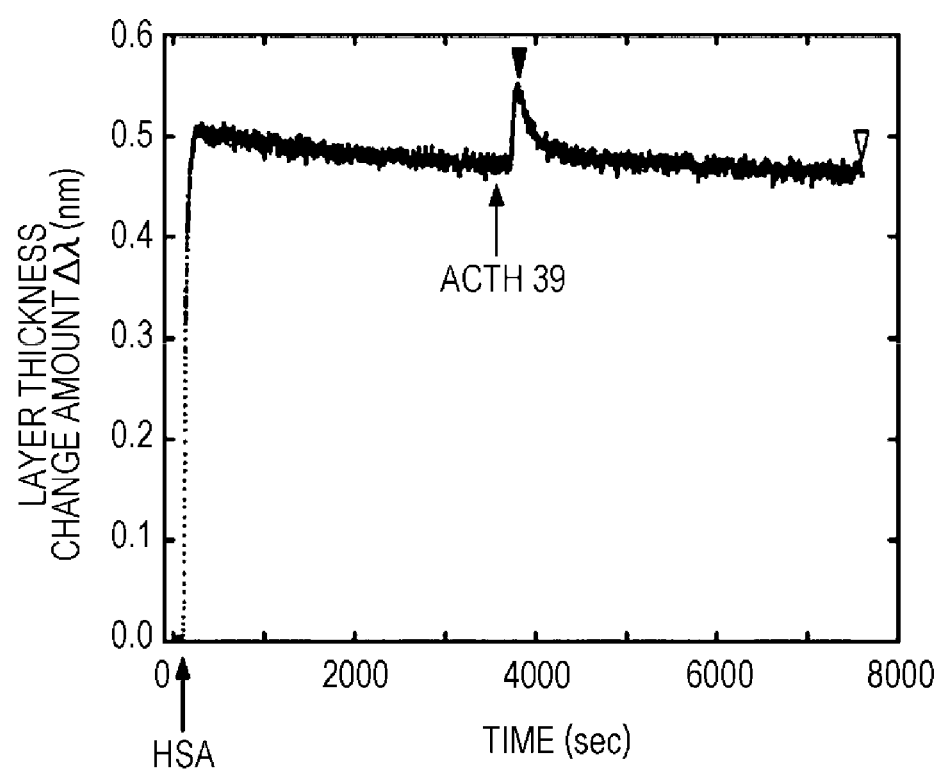
FIG. 4 is a sensorgram obtained in Example 1.

(4) Observation of Binding and Dissociation Between HSA and Peptide Based on Reflection Interference Spectroscopy 30 minutes after attachment of HSA to the surface of the substrate in Example 1 (2), 100 μL of the peptide solution obtained in Example 1 (3) was injected into the flow path at a flow rate of 100 μL/min. The wavelength variation Δλ of the bottom wavelength of the spectral reflectivity curve of the reflected light (the layer thickness change amount Δλ) when the flow path was irradiated with white light was measured with time, whereby a sensorgram was obtained. FIG. 4 shows an example of the sensorgram obtained by using ACTH39 as the peptide. In this figure, the arrow of HSA indicates the time of the injection of the HSA solution and the arrow of ACTH39 indicates the time of the injection of the ACTH39 peptide solution. In the figure, the black triangle indicates the start of the dissociation and the white triangle indicates the end of the dissociation.

The results in FIG. 4 indicate that the layer thickness change amount Δλ increases immediately after the injection of the HSA solution into the flow path. Further, the result indicates that, during the period from the injection of the HSA solution to the injection of the ACTH39 peptide solution, a constant layer thickness change amount Δλ is maintained. Therefore, this result suggests that HSA is stably immobilized on the surface of the substrate. On the other hand, when the ACTH39 peptide solution is injected into the flow path, the layer thickness change amount once increases. Thereafter, the layer thickness change amount decreases to the same extent as the layer thickness change amount before the injection of the ACTH39 peptide solution. Therefore, this result suggests that ACTH39 binds to HSA to form a complex of ACTH39 and HSA, and then dissociates from HSA.

Figure 5:
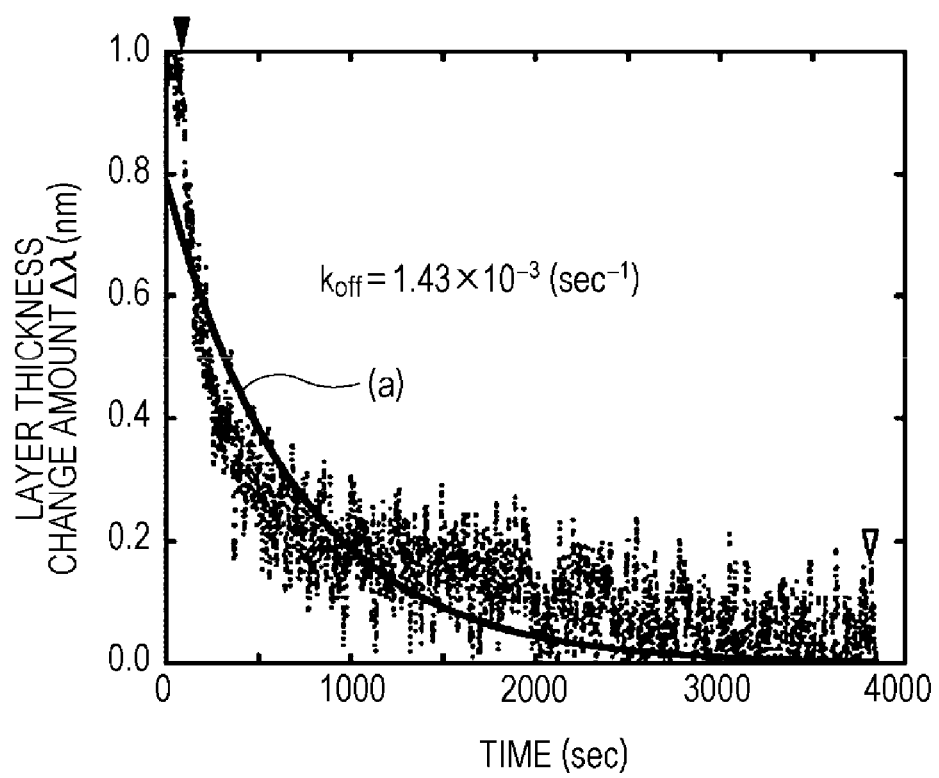
FIG. 5 is a sensorgram obtained in Example 1.

(5) Calculation of Dissociation Rate Constant and Maximum Value of Layer Thickness Change Amount The dissociation rate constant was calculated by the following procedure. A sensorgram showing the time-dependent change of the layer thickness change amount $\Delta\lambda$ during the period from the start to the end of the dissociation of the peptide is first created. Then, the obtained sensorgram is subjected to least-square-based curve fitting using software for statistical analysis and graph generation [HU-LINKS Inc., product name: Kaleida Graph] to obtain an approximate curve (a) of the sensorgram. FIG. 5 shows an example of the sensorgram subjected to curve fitting. The obtained approximate curve (a) is a curve represented by Equation (I):

[Equation 1]

$$\Delta\lambda = a \times e^{-k_1 \cdot t} b \times e^{-k_2 \cdot t} \quad (I)$$

(wherein, $\Delta\lambda$ represents a layer thickness change amount, a, b, $k_1$, and $k_2$ represent arbitrary numbers determined by curve fitting, and t represents elapsed time). When the a value in Equation (I) is higher than the b value (a>b), the $k_1$ value is used as the dissociation rate constant $k_{off}$ of the peptide. When the a value is lower than the b value (a<b), the $k_2$ value is used as the dissociation rate constant $k_{off}$ of the peptide. The dissociation rate constant $k_{off}$ of the peptide in the sensorgram illustrated in FIG. 5 is calculated as $1.43 \times 10^{-3}$ sec$^{-1}$.

The sensorgram of each of the peptides of ACTH24, ACTH39, ACTH41, SA21, ITIH4, glucagon, BNP, fibrinogen α, (Arg)10, and (His)20 was subjected to curve fitting to obtain an approximate curve of the sensorgram. The dissociation rate constant $k_{off}$ of each of the peptides was calculated from the equation representing the obtained approximate curve according to the above procedure. As a result, each of the peptides tended to have different dissociation rate constants $k_{off}$ depending on the type of peptides.

The maximum value of the layer thickness change amount (hereinafter also referred to as "maximum layer thickness change amount") was calculated using the equation representing the approximate curve of the sensorgram of each of the peptides. As a result, each of the peptides tended to have the maximum layer thickness change amount when bound to HSA.

(6) Determination of Dissociation Mode of Peptides from HSA

The dissociation mode of the peptide from the HSA can be determined based on the criteria that the b value of Equation (I) is lower than the predetermined threshold and the b value of Equation (I) is the predetermined threshold or more. Specific determination criteria used in this example are as follows.
<Determination Criteria>
When the b value is lower than 0.241 (b<0.241), the dissociation mode of the peptide from the protein is the "single dissociation mode."

When the b value is 0.241 or more (b≥0.241), the dissociation mode of the peptide from the protein is the "multiple dissociation mode."

Therefore, these results show that, depending on the type of peptides, the following items are different: (I) the dissociation rate constant $k_{off}$ when a peptide dissociates from a protein on a solid phase carrier having a surface on which the protein binding to the peptide is immobilized (hereinafter also referred to as "protein sensor chip") (first information); (II) the maximum layer thickness change amount of the protein sensor chip (second information); and (III) whether the dissociation mode of the peptide and the protein is either the single dissociation mode or the multiple dissociation mode (third information).

The above results suggest that, based on the first to third information on a known peptide and the first to third information on a target peptide, the process of determining the type of the target peptide (for example, determining whether the target peptide is the specific known peptide) can be performed.

(7) One Type of Known Peptide Map Formation

Figure 6:
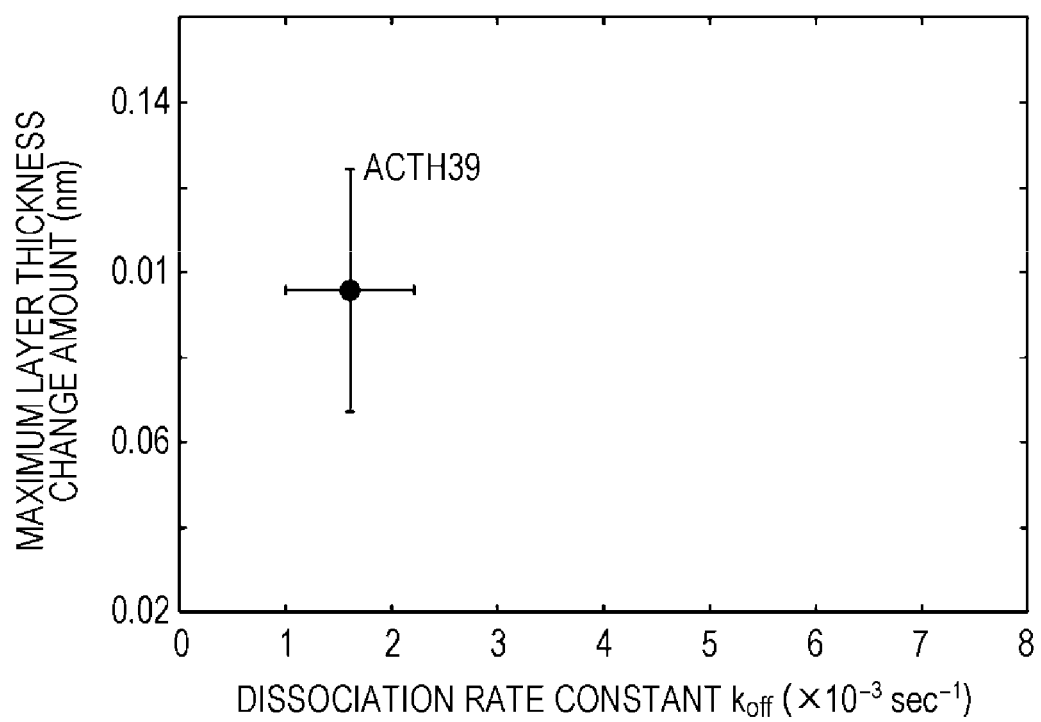
FIG. 6 is a peptide map of a type of known peptide obtained in Example 1.

Based on the dissociation rate constant $k_{off}$ (first information), the maximum layer thickness change amount (second information), and the type of the dissociation mode (third information) when the HSA sensor chip and one type of peptide (ACTH39) as the known peptide were used, a peptide map of one type of known peptide was formed. The results are shown in FIG. 6. In this figure, a black circle represents a multiple dissociation mode.

In the peptide map, the dissociation rate constant $k_{off}$ (the first information) is considered to be an index of the affinity between the HSA and the peptide. The maximum layer thickness change amount (the second information) is considered to be an index of the magnitude of the structural change of a complex of the HSA and the peptide. The single dissociation mode or the multiple dissociation mode (the third information) is considered to be an index of the difference in the dissociation mode of the peptide from the HSA.

The use of the peptide map makes the comparison in the first to third information on a known peptide easy. Therefore, it is suggested that the type of the peptide can be easily determined according to the peptide map based on the first to third information on one type of known peptide.

Example 2

Figure 7:
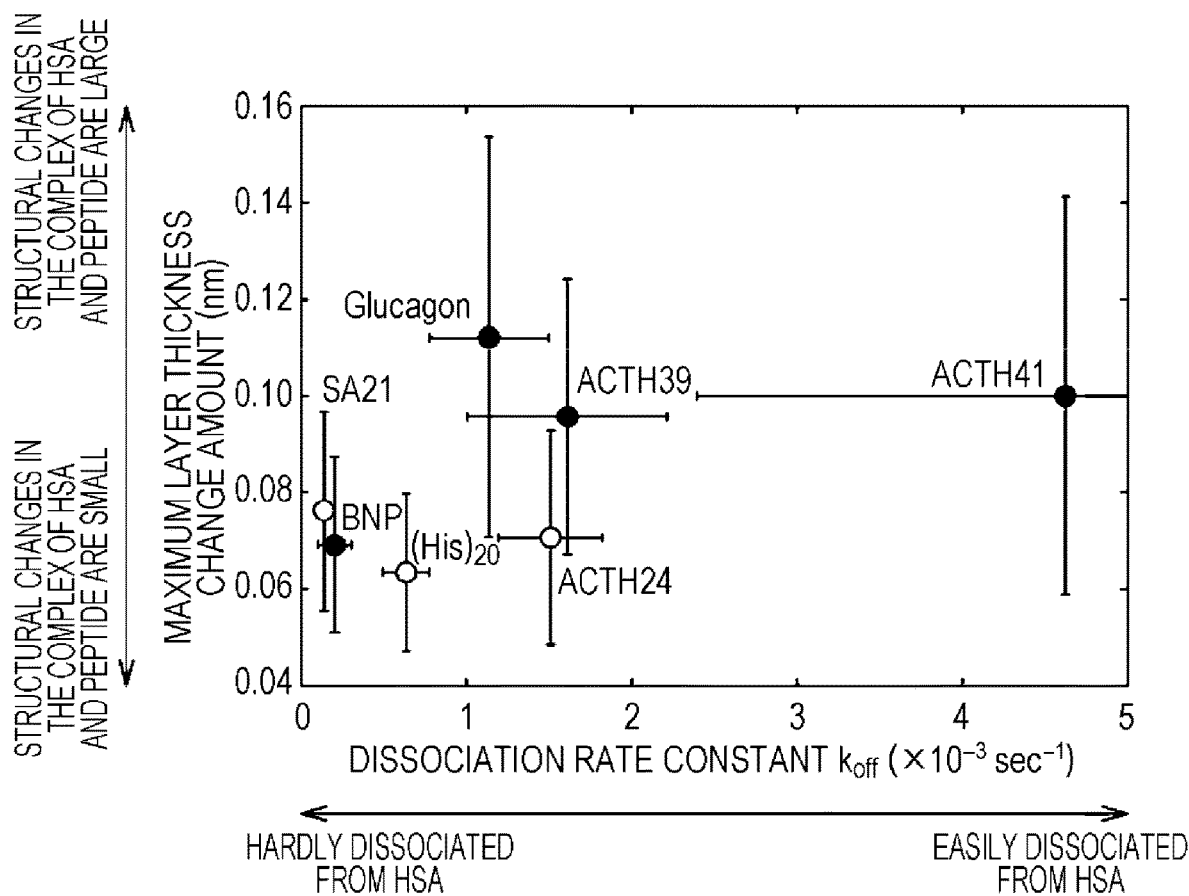
FIG. 7 is a peptide map of multiple types of known peptides obtained in Example 1.

The same operation as Example 1 was performed using the HSA sensor chip and multiple types of known peptides [ACTH24, ACTH39, ACTH41, SA21, ITIH4, glucagon, BNP, fibrinogen α, (Arg)10, and (His)20] to obtain the dissociation rate constant $k_{off}$ (first information), the maximum layer thickness change amount (second information), and the type of the dissociation mode (third information). Based on the first to third information on multiple types of known peptides when the HSA sensor chip and multiple types of known peptides [ACTH24, ACTH39, ACTH41, SA21, ITIH4, glucagon, BNP, fibrinogen α, (Arg)10, and (His)20] were used, a peptide map for the multiple types of known peptides was formed. The results are shown in FIG. 7. In the drawing, each white circle represents a single dissociation mode and each black circle represents a multiple dissociation mode.

As shown in FIG. 7, in the peptide map based on the first to third information, each of the multiple types of known peptides is distinguishably separated and plotted. Therefore, it is suggested that the type of the peptide can be easily determined according to the peptide map based on the first to third information on multiple types of known peptides.

Example 3

(1) Preparation of Test Sample

A powder of each of the peptides [ACTH24, ACTH39, ACTH41, SA21, ITIH4, glucagon, BNP, fibrinogen α, (Arg) 10, and (His)20] [manufactured by Biologica Co, Ltd.] was dissolved in purified desalting water to prepare a peptide solution. Then, the obtained peptide solution was diluted with 0.1 M sodium phosphate buffer so as to have a concentration of peptide of 2 μM and a peptide solution was prepared. To a 1.5-mL tube having a label on which each peptide name had been described, 500 μL of the corresponding peptide solution was poured.

(2) Random Selection of Test Sample

A first test participant randomly swapped the peptide name labels of the tubes obtained in Example 3 (1) for numbered labels (1 to 10). In the blind test, only the first test participant knew the correspondence between the number of the labels and the type of peptide solutions. Subsequently, a second test participant randomly selected three numbers from the total number of 1 to 10. As test samples, three types of peptide solutions (Nos. 2, 6, and 10) were extracted.

(3) Collection of First to Third Information

The same operation as Example 1 (2) was performed so as to attach HSA to the surface of a substrate and an HSA sensor chip was obtained. 30 minutes after attachment of HSA to the substrate, 100 μL of a test sample randomly selected from the three types of test samples in Example 3 (1) was injected into a flow path formed between the HSA sensor chip and the flow cell at a flow rate of 100 μL/min. The wavelength variation Δλ of the bottom wavelength of the spectral reflectivity curve of the reflected light (the layer thickness change amount Δλ) when the flow path was irradiated with white light was measured with time, whereby a sensorgram was obtained. A series of tests for forming an HSA sensor chip and measuring the wavelength variation Δλ (the layer thickness change amount Δλ) was carried out 4 times or more. The obtained sensorgram was subjected to least-square-based curve fitting using software for statistical analysis and graph generation [HULINKS Inc., product name: Kaleida Graph] to obtain an approximate curve of the sensorgram. The same operation as Example 1 was performed using the obtained approximate curve and the equation representing the approximate curve to obtain first to third information. The first information was obtained by calculating an average and standard deviation for the dissociation rate constants $k_{off}$ obtained from the tests performed four times or more. The second information was obtained by calculating an average and standard deviation for the maximum layer thickness change amounts obtained from the tests performed four times or more.

(4) Determination of Type of Target Peptide

Based on the first to third information on multiple types of known peptides obtained in Example 3 (3) and the first to third information on a target peptide contained in a test sample, the type of the target peptide was determined by the following two methods.

In the first method, the first to third information on multiple types of known peptides was compared with the first to third information on a target peptide contained in a test sample. Subsequently, based on the determination criteria described below, it was examined whether the target peptide was the specific known peptide and the type of the target peptide was determined.

<Determination Criteria>

(I) the dissociation rate constant $k_{off}$ of the target peptide is equal or similar to the dissociation rate constant $k_{off}$ of the specific known peptide (the value calculated by Equation (II) is 0.315 or less);

(II) the maximum layer thickness change amount of the protein sensor chip when using the target peptide is equal or similar to the maximum layer thickness change amount of the specific known peptide; and (III) the dissociation mode of the target peptide and the protein is equal to the dissociation mode of the specific known peptide and the protein (the single dissociation mode or the multiple dissociation mode).

In the second method, a peptide map of known peptides was formed based on the first to third information. Then, the first to third information on a target peptide contained in a test sample was plotted on the obtained peptide map. Thereafter, a known peptide corresponding to a coordinate point located at the nearest distance from the coordinate point corresponding to the target peptide was identified.

As a result of the first method, the target peptide contained in the test sample No. 2 was determined to be ITIH4. The target peptide contained in the test sample No. 6 was determined to be ACTH39. The test sample No. 10 was determined to be BNP. Subsequently, the first participant compared the obtained determination result with the type of peptide solutions actually used as the test samples. As a result, it is shown that the determination result is correct.

Figure 8A:
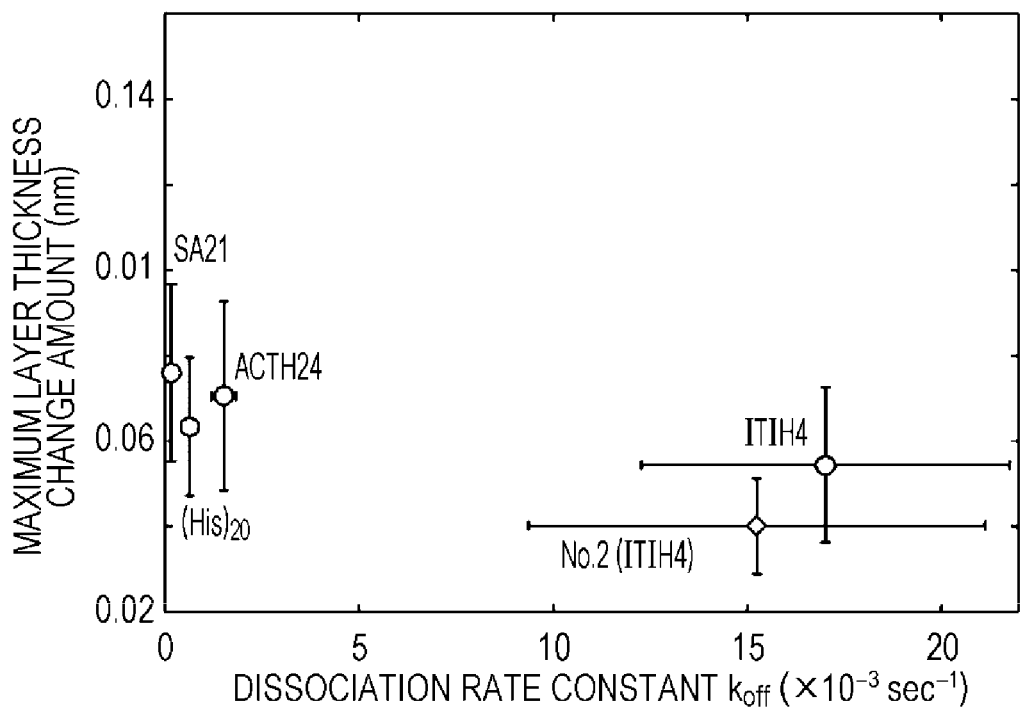
FIGS. 8A and 8B are explanatory views illustrating determination results obtained in Example 1.
Figure 8B:
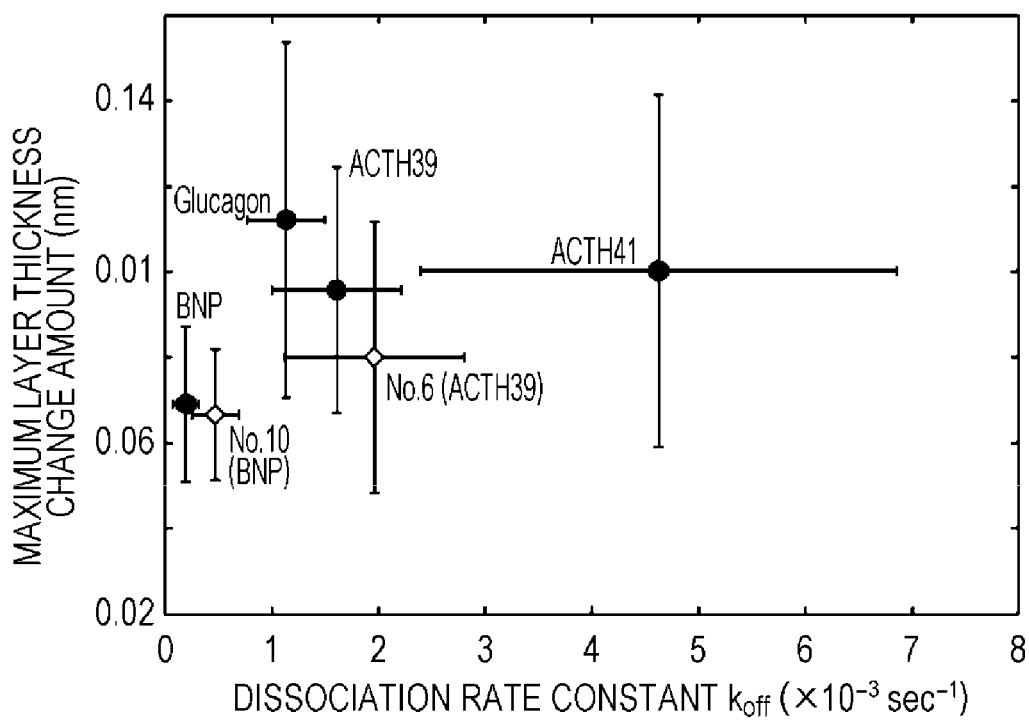

FIG. 8 shows the results of the second method. FIG. 8 (A) shows a peptide map of known peptides dissociating in the single dissociation mode from HSA, and FIG. 8 (B) shows a peptide map of known peptides dissociating in the multiple dissociation mode from HSA. In the drawings, each white circle represents a single dissociation mode, each black circle represents a multiple dissociation mode, and each rectangle represents a target peptide. From the results shown in FIG. 8, the coordinate point of the target peptide contained in the test sample No. 2 is located near the coordinate point of ITIH4. Thus, the target peptide contained in the test sample No. 2 was determined to be ITIH4. The coordinate point of the target peptide contained in the test sample No. 6 is located near the coordinate point of ACTH39. Thus, the target peptide contained in the test sample No. 6 was determined to be ACTH39. The coordinate point of the target peptide contained in the test sample No. 10 is located near the coordinate point of BNP. The test sample No. 10 was determined to be BNP. Subsequently, the first participant compared the obtained determination result with the type of peptide solutions actually used as the test samples. As a result, it is shown that the determination result is correct.

The above results show that the type of the peptide can be easily determined according to the peptide map based on the first to third information on multiple types of known peptides.

Comparative Example 1

The same operation as the second method in Example 3 was performed except that the first information and the second information were used in place of the first to third information in Example 3 (4), and the type of the target peptide was determined. The results are shown in FIG. 9. In this figure, the graph (b) is a partially enlarged view of the graph (a).

The results in FIG. 9 show that the coordinate point of the target peptide in the test sample No. 6 is located near both of the coordinate point of ACTH24 and the coordinate point of ACTH39. Further, the coordinate point of the target peptide in the test sample No. 10 is located near both of the coordinate point of BNP and the coordinate point of (His)20. These results show that it is difficult to determine the type of the peptide based on only the first information and the second information.

Example 4

(1) Preparation of Whole Blood Solution

In Example 4, human whole blood [manufactured by Tokyo Future Style, Inc.] was used as a protein binding to a peptide. Human whole blood was subjected to 10000-20000-fold dilution with 0.1 M sodium phosphate buffer (pH 6.9) to prepare a whole blood solution.

(2) Production of Whole Blood Sensor Chip

A substrate [product name: sensor chip (unmodified) for MI-Affinity (registered trademark), model name: LCF-01, manufactured by Konica Minolta, Inc.] and a flow cell [product name: MI-Affinity (registered trademark) flow cell, model name: LCF-01, manufactured by Konica Minolta, Inc.] were mounted on a device for measuring intermolecular interaction [Konica Minolta, Inc., product name: MI-Affinity (registered trademark)].

Figure 10A:
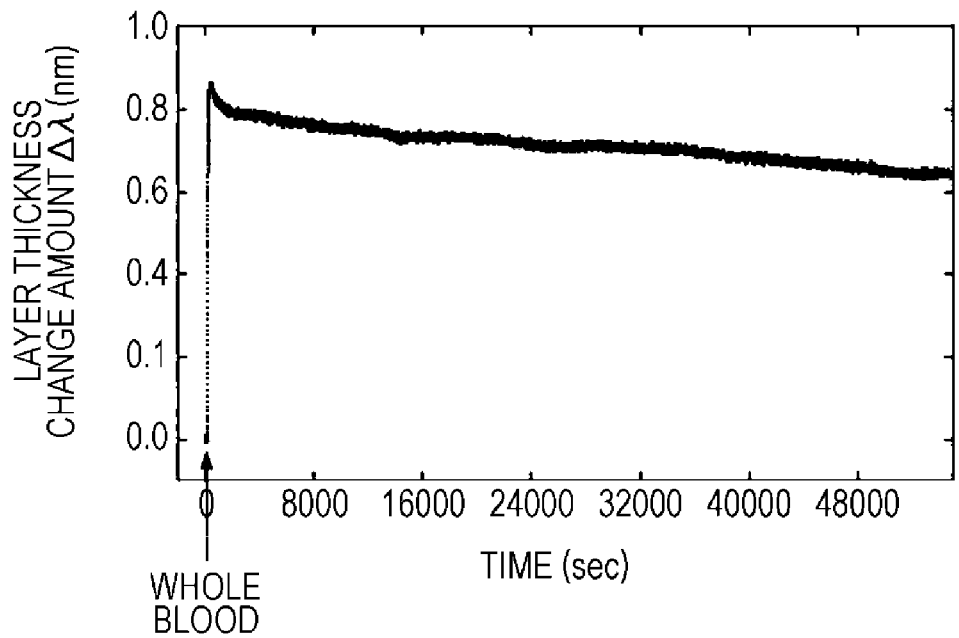
FIG. 10A is a sensorgram illustrating changes in the layer thickness on a support from the time whole blood is immobilized on a substrate and FIG. 10B is a peptide map obtained in Example 4.

Then, a running buffer (0.1 M sodium phosphate buffer (pH 6.9)) was injected into a flow path formed between the substrate and the flow cell at a flow rate of 50 μL/min for 30 minutes or more so as to equilibrate the surface of the substrate. Thereafter, 100 μL of the whole blood solution obtained in Example 4 (1) was injected into the flow path at a flow rate of 50 μL/min so as to attach the whole blood component to the surface of the substrate. In injecting the running buffer or the whole blood solution, a liquid feeding pump for high-performance liquid chromatograph [product name: Prominence UFLC, manufactured by Shimadzu Corporation] and an autosampler [product name: Chromaster, manufactured by Hitachi, Ltd.] were used. As a result, a solid phase carrier having the whole blood component immobilized on the surface thereon (hereinafter also referred to as "whole blood sensor chip") was obtained. In injecting the whole blood solution into the flow path, the wavelength variation Δλ (the layer thickness change amount Δλ) of the bottom wavelength of the spectral reflectivity curve of the reflected light when the flow path was irradiated with white light was measured with time, whereby a sensorgram was obtained. The obtained sensorgram is shown in FIG. 10A. The obtained sensorgram was subjected to least-square-based curve fitting using software for statistical analysis and graph generation [HULINKS Inc., product name: Kaleida Graph] to obtain an approximate curve of the sensorgram. The same operation as Example 1 was performed using the obtained approximate curve and the equation representing the approximate curve to determine the dissociation rate constant $k_{off}$ of the whole blood component dissociating from the substrate.

The results in FIG. 10A show that the obtained sensorgram exhibited a constant wavelength variation Δλ (the layer thickness change amount Δλ) immediately after the injection of the whole blood solution into the flow path. Subsequently, the dissociation rate constant $k_{off}$ of the whole blood dissociating from the substrate was determined from the sensorgram. As a result, the dissociation of the whole blood from the substrate was hardly observed in the dissociation rate constant $k_{off}$ of the whole blood. Accordingly, the dissociation rate constant $k_{off}$ was not able to be calculated by curve fitting. However, the sensorgram shows that the whole blood was immobilized on the surface of the substrate for 56 hours or more. This suggests that the whole blood sensor chip has high storage stability and high practicability.

(3) Preparation of Peptide Solution

Amyloid β40 peptide (hereinafter referred to as "AB40"), amyloid β42 peptide (hereinafter referred to as "AB42"), ACTH24, ACTH15, ACTH39, ACTH41, dynorphin A or SA21 was dissolved in purified desalting water to prepare a peptide solution. Then, the obtained peptide solution was diluted with 0.1 M sodium phosphate buffer so as to have the peptide concentration shown in Table 2 and a peptide solution was prepared.

TABLE 2

| Known peptide | Concentration (μM) |
|---|---|
| AB40 | 0.5 |
| AB42 | 1 |
| ACTH24 | 0.5 |
| ACTH15 | 10 |
| ACTH39 | 2 |
| ACTH41 | 0.5 |
| Dynorphin A | 0.5 |
| SA21 | 2 |

(4) Collection of First to Third Information

The same operation as Example 1 was performed using the whole blood sensor chip obtained in Example 4 (2) and each of the peptide solutions obtained in Example 4 (3) to obtain the dissociation rate constant $k_{off}$ (first information), the maximum layer thickness change amount (second information), and the type of the dissociation mode (third information). As a result, the first information, the second information, and the third information were different depending on the type of peptides. These results suggest that the type of the target peptide can be easily determined by using the whole blood sensor chip.

(5) Peptide Map Formation

Figure 10B:
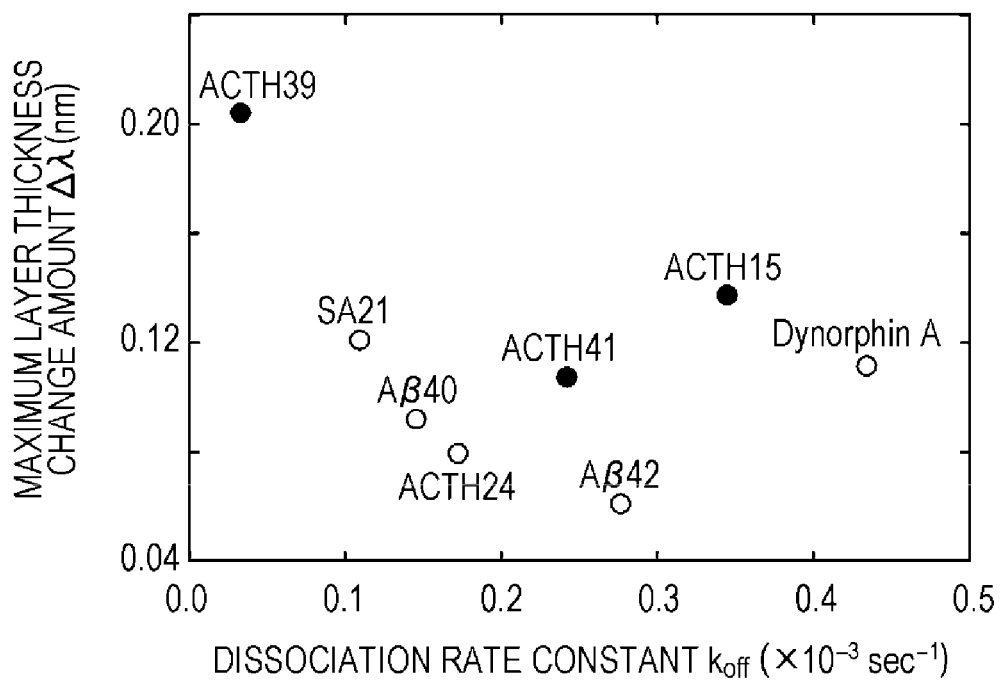

Based on the first to third information obtained in Example 4 (4), a map of multiple types of known peptides [AB40, AB42, ACTH24, ACTH15, ACTH39, ACTH41, dynorphin A, and SA21] was formed. The results are shown in FIG. 10 (B). In the drawing, each white circle represents a single dissociation mode and each black circle represents a multiple dissociation mode.

As shown in FIG. 10 (B), in the peptide map formed using the whole blood sensor chip, each of the multiple types of known peptides is distinguishably separated and plotted. Therefore, it is suggested that the type of the peptide can be easily determined according to the peptide map formed using the whole blood sensor chip.

Example 5

(1) Preparation of Human γ-Globulin Solution

In Example 5, human γ-globulin (hereinafter referred to as "HγG") [manufactured by Wako Pure Chemical Industries, Ltd.] was used as a protein binding to a peptide. HγG was dissolved in purified desalting water to prepare an HγG solution. The HγG solution obtained was diluted with 0.1 M sodium phosphate buffer (pH 6.9) so as to have a concentration of HγG of 50 μg/mL and an HγG solution was prepared.

(2) Production of HγG Sensor Chip

Figure 11A:
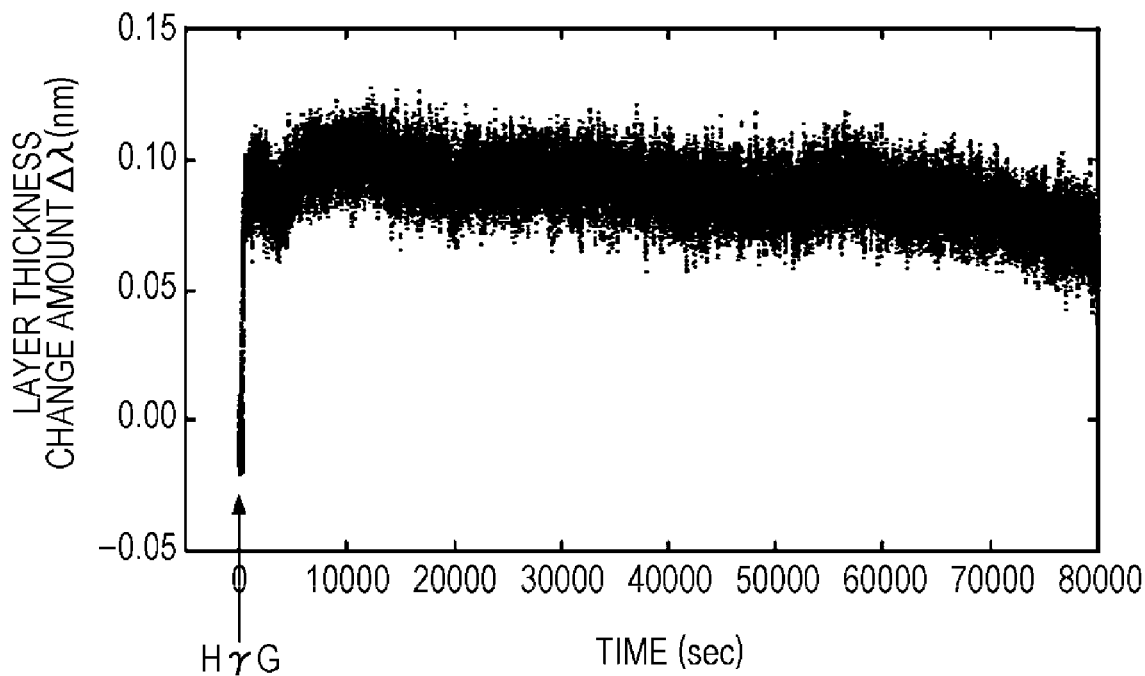
FIG. 11A is a sensorgram illustrating changes in the layer thickness on a support from the time human γ-globulin is immobilized on a substrate and FIG. 11B is a peptide map obtained in Example 5.

An HγG sensor chip was produced by performing the same operation as Example 4 (3) except that the HγG solution was used in place of the whole blood solution in Example 4 (2). In injecting the HγG solution into the flow path, the wavelength variation Δλ (the layer thickness change amount Δλ) of the bottom wavelength of the spectral reflectivity curve of the reflected light when the flow path was irradiated with white light was measured with time, whereby a sensorgram was obtained. The obtained sensorgram is shown in FIG. 11A.

Figure 11B:
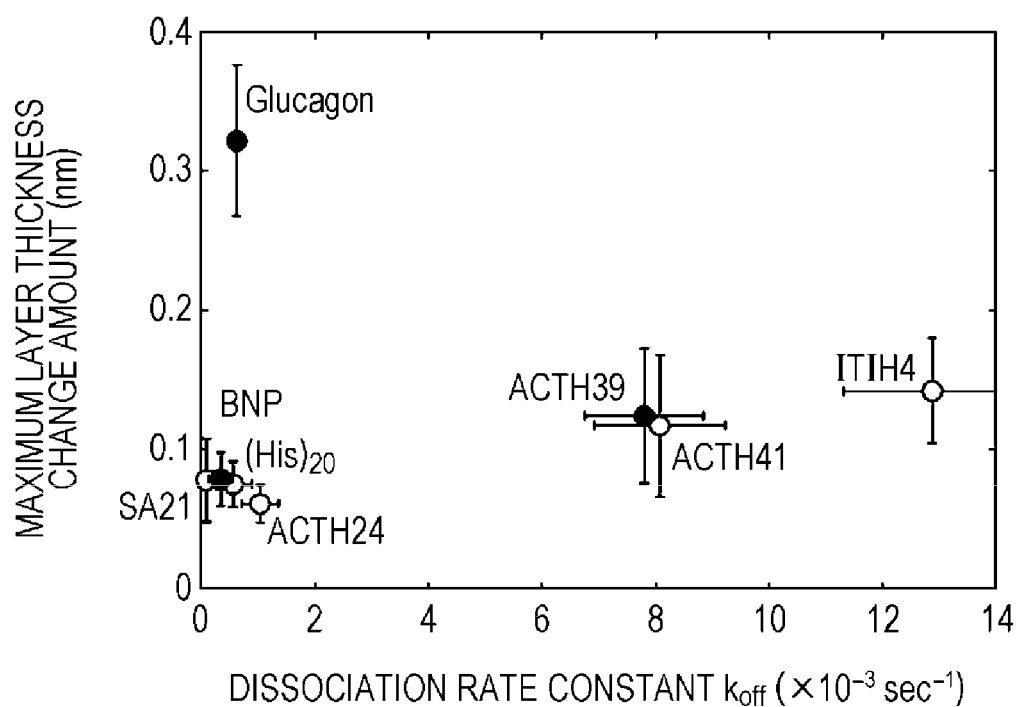

The dissociation of HγG from the substrate was hardly observed in the results in FIG. 11 (A). Accordingly, it was not able to calculate the dissociation rate constant $k_{off}$. However, the sensorgram shows that the HγG was immobilized on the surface of the substrate for 56 hours or more. This suggests that the HγG sensor chip has high storage stability and high practicability.

(3) Preparation of Peptide Solution

AB40, AB42, ACTH24, ACTH15, ACTH39, ACTH41, dynorphin A or SA21 was dissolved in purified desalting water to prepare a peptide solution. Then, the obtained peptide solution was diluted with 0.1 M sodium phosphate buffer so as to have a concentration of peptide of 10 μM and a peptide solution was prepared.

(4) Collection of First to Third Information

The same operation as Example 1 was performed using the HγG sensor chip obtained in Example 5 (2) and each of the peptide solutions obtained in Example 5 (3) to obtain the dissociation rate constant $k_{off}$ (first information), the maximum layer thickness change amount (second information), and the type of the dissociation mode (third information). As a result, the first information, the second information, and the third information were different depending on the type of peptides. These results suggest that the type of the target peptide can be easily determined by using the HγG sensor chip.

(5) Peptide Map Formation

Based on the first to third information obtained in Example 5 (4), a map of multiple types of known peptides [AB40, AB42, ACTH24, ACTH15, ACTH39, ACTH41, dynorphin A, and SA21] was formed. The results are shown in FIG. 11 (B). In the drawing, each white circle represents a single dissociation mode and each black circle represents a multiple dissociation mode.

As shown in FIG. 11 (B), in the peptide map formed using the HγG sensor chip, each of the multiple types of known peptides is distinguishably separated and plotted. Therefore, it is suggested that the type of the peptide can be easily determined according to the peptide map formed using the HγG sensor chip.

Example 6

(1) Preparation of Transthyretin Solution

In Example 6, transthyretin [manufactured by AbD Serotec] was used as a protein binding to a peptide. Transthyretin was dissolved in purified desalting water to prepare a transthyretin solution. Then, the obtained transthyretin solution was diluted with 0.1 M sodium phosphate buffer (pH 6.9) so as to have a concentration of transthyretin of 0.2 μM and a transthyretin solution was prepared.

(2) Production of Transthyretin Sensor Chip

A transthyretin sensor chip was produced by performing the same operation as Example 4 (3) except that the transthyretin solution was used in place of the whole blood solution in Example 4 (2). In injecting the transthyretin solution into the flow path, the wavelength variation Δλ (the layer thickness change amount Δλ) of the bottom wavelength of the spectral reflectivity curve of the reflected light when the flow path was irradiated with white light was measured with time, whereby a sensorgram was obtained. The obtained sensorgram is shown in FIG. 12A.

Figure 12A:
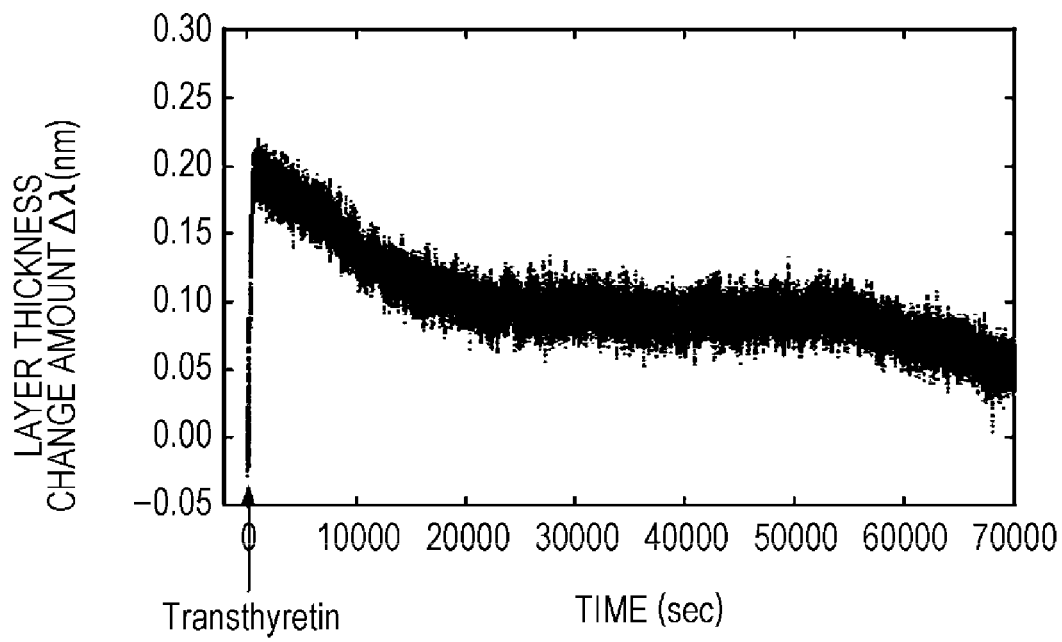
FIG. 12A is a sensorgram illustrating changes in the layer thickness on a support from the time transthyretin is immobilized on a substrate and FIG. 12B is a peptide map obtained in Example 6.

The results in FIG. 12A show that the obtained sensorgram exhibited a constant wavelength variation Δλ (the layer thickness change amount Δλ) immediately after the injection of the transthyretin solution into the flow path. Subsequently, the dissociation rate constant $k_{off}$ of transthyretin dissociating from the substrate was determined from the sensorgram. As a result, the dissociation of transthyretin from the substrate was hardly observed. Accordingly, it was not able to calculate the dissociation rate constant $k_{off}$. However, the sensorgram shows that transthyretin was immobilized on the surface of the substrate for 17 hours or more. This suggests that the transthyretin sensor chip has high storage stability and high practicability.

(3) Preparation of Peptide Solution

AB40, AB42, ACTH24, ACTH15, ACTH39, ACTH41, dynorphin A or SA21 was dissolved in purified desalting water to prepare a peptide solution. Then, the obtained peptide solution was diluted with 0.1 M sodium phosphate buffer so as to have the peptide concentration shown in Table 3 and a peptide solution was prepared.

TABLE 3

| Known peptide | Concentration (μM) |
| --- | --- |
| AB40 | 0.5 |
| AB42 | 10 |
| ACTH24 | 10 |
| ACTH15 | 10 |

TABLE 3-continued

| Known peptide | Concentration (μM) |
|---|---|
| ACTH39 | 0.5 |
| ACTH41 | 0.5 |
| Dynorphin A | 10 |
| SA21 | 0.5 |

(4) Collection of First to Third Information

The same operation as Example 1 was performed using the transthyretin sensor chip obtained in Example 6 (2) and each of the peptide solutions obtained in Example 6 (3) to obtain the dissociation rate constant $k_{off}$ (first information), the maximum layer thickness change amount (second information), and the type of the dissociation mode (third information). As a result, the first information, the second information, and the third information were different depending on the type of peptides. These results suggest that the type of the target peptide can be easily determined by using the transthyretin sensor chip.

(5) Peptide Map Formation

Figure 12B:
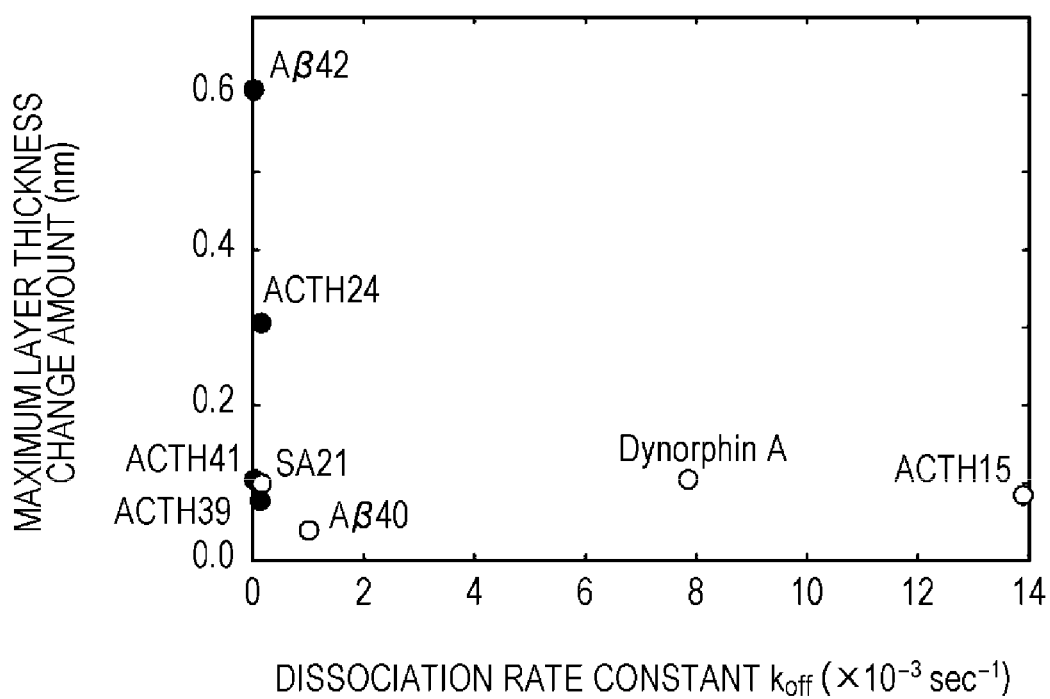

Based on the first to third information obtained in Example 6 (4), a peptide map of multiple types of known peptides [AB40, AB42, ACTH24, ACTH15, ACTH39, ACTH41, dynorphin A, and SA21] was generated. The results are shown in FIG. 12 (B). In the drawing, each white circle represents a single dissociation mode and each black circle represents a multiple dissociation mode.

As shown in FIG. 12 (B), in the peptide map formed using the transthyretin sensor chip, each of the multiple types of known peptides is distinguishably separated and plotted. Therefore, it is suggested that the type of the peptide can be easily determined according to the peptide map formed using the transthyretin sensor chip.

Example 7

(1) Preparation of Bovine Serum Albumin Solution

In Example 7, bovine serum albumin (hereinafter referred to as "BSA", manufactured by Sigma-Aldrich Co. LLC.) was used as a protein binding to a peptide. A BSA solution was prepared by dissolving BSA in purified desalting water so as to have a concentration of 0.5 μM to 1 μM.

(2) Production of BSA Sensor Chip

A BSA sensor chip was produced by performing the same operation as Example 4 (3) except that the BSA solution was used in place of the whole blood solution in Example 4 (2). In injecting the BSA solution into the flow path, the wavelength variation Δλ (the layer thickness change amount Δλ) of the bottom wavelength of the spectral reflectivity curve of the reflected light when the flow path was irradiated with white light was measured with time, whereby a sensorgram was obtained. The obtained sensorgram is shown in FIG. 13A.

Figure 13A:
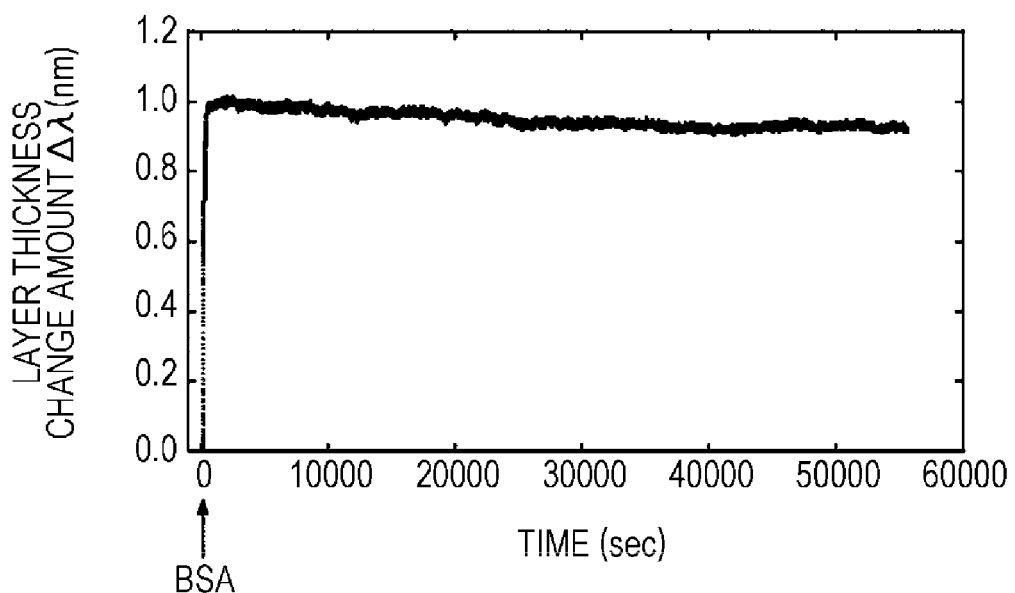
FIG. 13A is a sensorgram illustrating changes in the layer thickness on a support from the time BSA is immobilized on a substrate and FIG. 13B is a peptide map obtained in Example 7.

The results in FIG. 13A show that the obtained sensorgram exhibited a constant wavelength variation Δλ (the layer thickness change amount Δλ) immediately after the injection of the BSA solution into the flow path. Subsequently, the dissociation rate constant $k_{off}$ of BSA dissociating from the substrate was determined from the sensorgram. As a result, the dissociation of BSA from the substrate was hardly observed. Accordingly, it was not able to calculate the dissociation rate constant $k_{off}$. However, the sensorgram shows that BSA was immobilized on the surface of the substrate for 111 hours or more. This suggests that the BSA sensor chip has high storage stability and high practicability.

(3) Preparation of Peptide Solution

ACTH24, AB40, SA21, dynorphin A, kininogen, ITIH4, fibrinogen, or glucagon was dissolved in purified desalting water to prepare a peptide solution. Then, the obtained peptide solution was diluted with 0.1 M sodium phosphate buffer so as to have the peptide concentration shown in Table 4 and a peptide solution was prepared.

TABLE 4

| Known peptide | Concentration (μM) |
|---|---|
| AB40 | 5 |
| ACTH24 | 5 |
| Dynorphin A | 5 |
| SA21 | 10 |
| Kininogen | 10 |
| ITIH4 | 10 |
| Fibrinogen α | 10 |
| Glucagon | 10 |

(4) Collection of First to Third Information

The same operation as Example 1 was performed using the BSA sensor chip obtained in Example 7 (2) and each of the peptide solutions obtained in Example 7 (3) to obtain the dissociation rate constant $k_{off}$ (first information), the maximum layer thickness change amount (second information), and the type of the dissociation mode (third information). As a result, the first information, the second information, and the third information were different depending on the type of peptides. These results suggest that the type of the target peptide can be easily determined by using the BSA sensor chip.

(5) Peptide Map Formation

Figure 13B:
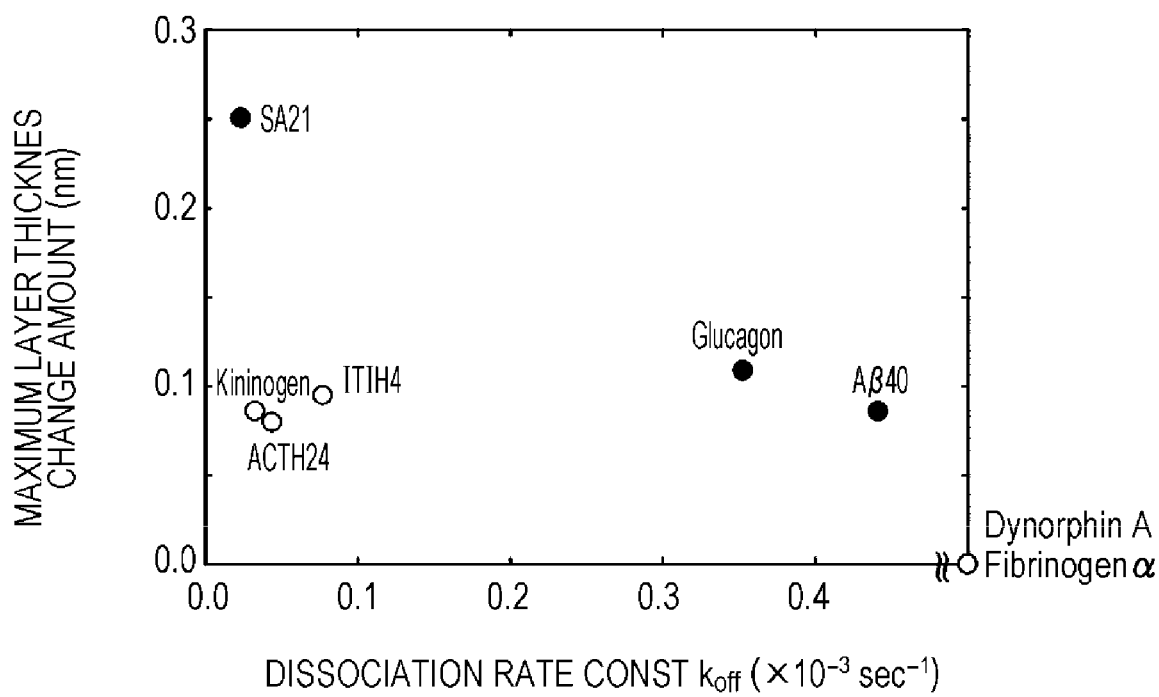

Based on the first to third information obtained in Example 7 (4), a peptide map of multiple types of known peptides [ACTH24, AB40, SA21, dynorphin A, kininogen, ITIH4, fibrinogen, and glucagon] was generated. The results are shown in FIG. 13 (B). In the drawing, each white circle represents a single dissociation mode and each black circle represents a multiple dissociation mode.

As shown in FIG. 13 (B), in the peptide map formed using the BSA sensor chip, each of the multiple types of known peptides is distinguishably separated and plotted. Therefore, it is suggested that the type of the peptide can be easily determined according to the peptide map formed using the BSA sensor chip.

Example 8

(1) Preparation of Heat-Denatured Bovine Serum Albumin Solution

In Example 8, heat-denatured bovine serum albumin (hereinafter referred to as "heat-denatured BSA") was used as a protein binding to a peptide. A powder of BSA (manufactured by Sigma-Aldrich Co. LLC.) was dissolved in purified desalting water so as to have a concentration of 1.0% by mass. The obtained solution was heated in an autoclave at 110° C. for 15 minutes to prepare heat-denatured BSA. A heat-denatured BSA solution was prepared by dissolving the heated solution in purified desalting water so as to have a concentration of heat-denatured BSA of 0.2 µM to 1 µM.

(2) Production of Heat-Denatured BSA Sensor Chip

A heat-denatured BSA sensor chip was produced by performing the same operation as Example 4 (3) except that the heat-denatured BSA solution was used in place of the whole blood solution in Example 4 (2). In injecting the heat-denatured BSA solution into the flow path, the wavelength variation Δλ (the layer thickness change amount Δλ) of the bottom wavelength of the spectral reflectivity curve of the reflected light when the flow path was irradiated with white light was measured with time, whereby a sensorgram was obtained. The obtained sensorgram is shown in FIG. 14A.

Figure 14A:
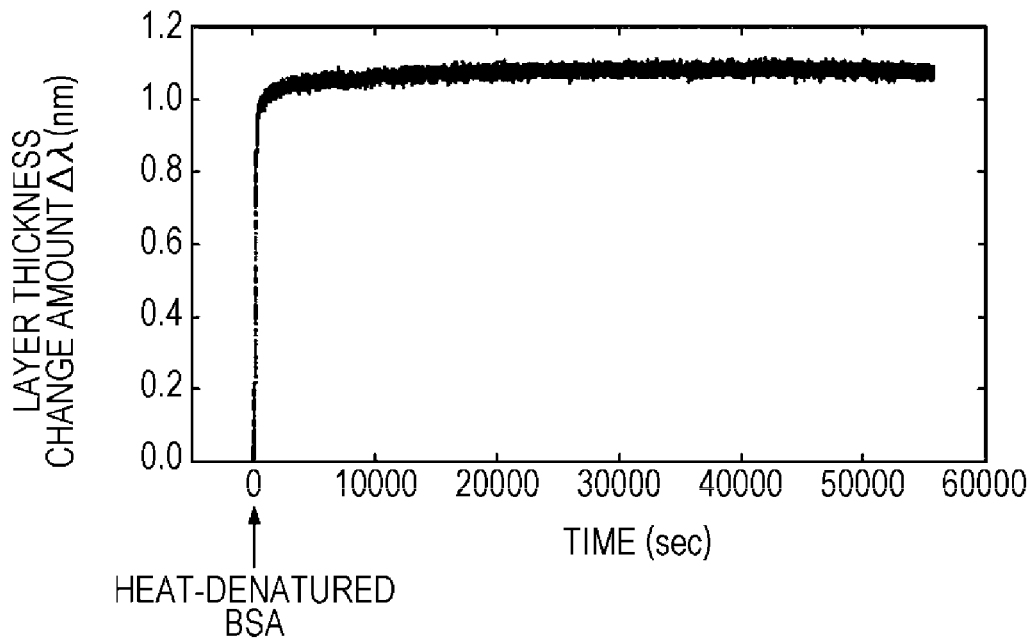
FIG. 14A is a sensorgram illustrating changes in the layer thickness on a support from the time when heat-denatured BSA is immobilized on a substrate and FIG. 14B is a peptide map obtained in Example 8.

The results in FIG. 14A show that the dissociation of the heat-denatured BSA from the substrate was hardly observed in the obtained sensorgram. Accordingly, it was not able to calculate the dissociation rate constant $k_{off}$. This suggests that the heat-denatured BSA sensor chip has high storage stability and high practicability.

(3) Collection of First to Third Information

The same operation as Example 1 was performed using the heat-denatured BSA sensor chip obtained in Example 8 (2) and each of the peptide solutions obtained in the same manner as Example 7 (3) to obtain the dissociation rate constant $k_{off}$ (first information), the maximum layer thickness change amount (second information), and the type of the dissociation mode (third information). As a result, the first information, the second information, and the third information were different depending on the type of peptides. These results suggest that the type of the target peptide can be determined by using the heat-denatured BSA sensor chip.

(5) Peptide Map Formation

Figure 14B:
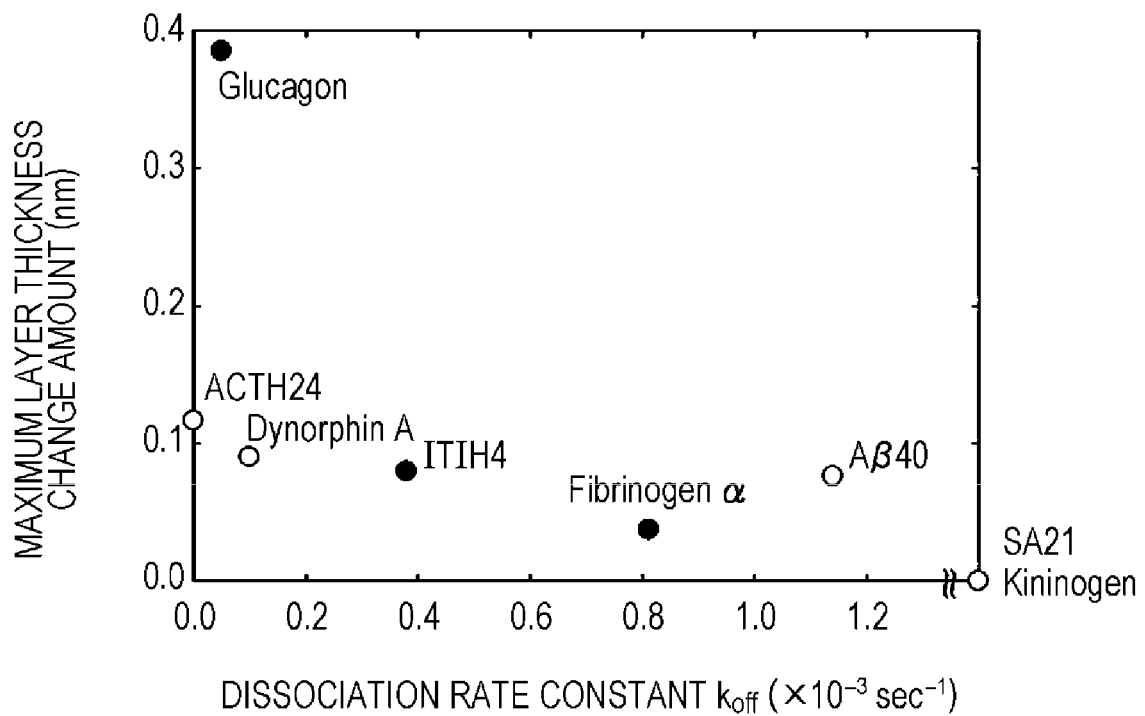

Based on the first to third information obtained in Example 8 (4), a peptide map of multiple types of known peptides [ACTH24, AB40, SA21, dynorphin A, kininogen, ITIH4, fibrinogen, and glucagon] was generated. The results are shown in FIG. 14 (B). In the drawing, each white circle represents a single dissociation mode and each black circle represents a multiple dissociation mode.

As shown in FIG. 14 (B), in the peptide map formed using the heat-denatured BSA sensor chip, each of the multiple types of known peptides is distinguishably separated and plotted. Therefore, it is suggested that the type of the peptide can be easily determined according to the peptide map formed using the heat-denatured BSA sensor chip.

The above results suggest that, based on a solid phase carrier having a surface on which a protein binding to a peptide is immobilized, the dissociation rate constant $k_{off}$ of the target peptide (first information), the maximum layer thickness change amount of the solid phase carrier (second information), and the type of the dissociation mode of the target peptide (third information) are used, whereby the type of the peptide can be easily determined without using a device requiring complicated operation such as a mass spectrometer.

Example 9

The same operation as Example 1 was performed using multiple types of peptides shown in Table 5 to obtain the dissociation rate constant $k_{off}$ of multiple types of peptides (first information), the maximum layer thickness change amount (second information), and the type of the dissociation mode (third information). In Table 5, "IS 13mer" represents the 237 to 249th fragments of the amino acid sequence of HSA. "ELN 11mer" represents the 548 to 558th fragments of the amino acid sequence of elastin.

TABLE 5

| Known peptide | Concentration of peptide during measurement (µM) | Amino acid sequence | SEQ ID NO: | The number of amino acid residues | Isoelectric point |
|---|---|---|---|---|---|
| (His) 3 | 1000 | HHH | — | 3 | 7 |
| Bradykinin | 50 | FPPGFSPFR | 16 | 9 | 12 |
| (His) 10 | 10 | HHHHHHHHHH | 17 | 10 | 7.4 |
| (Lys) 10 | 100 | KKKKKKKKKK | 18 | 10 | 11 |
| (Glu) 10 | 100 | EEEEEEEEEE | 19 | 10 | 3.5 |
| ELN 11 mer | 1 | GVPGLGVGAGV | 20 | 11 | 5.5 |
| IS 13 mer | 50 | AWAVARLSQRFPK | 21 | 13 | 12 |
| Dynorphin A | 10 | YGGFLRRIRPKLK | 14 | 13 | 11.7 |
| ACTH15 | 10 | YSMEHFRWGKPVGKK | 11 | 15 | 10 |
| Kininogen | 100 | HNLGHGHKHERDQGHGHQR | 15 | 19 | 8.8 |
| AB40 | 10 | DAEFRHDSGYEVHHQKLVFFAEDVGSNKGAIIGLMGGVV | 12 | 40 | 5.3 |

TABLE 5-continued

| Known peptide | Concentration of peptide during measurement (µM) | Amino acid sequence | SEQ ID NO: | The number of amino acid residues | Isoelectric point |
|---|---|---|---|---|---|
| AB42 | 2 | DAEFRHDSGYEVHHQKLVFFAEDVGSNKGAII GLMVGGVVIA | 13 | 42 | 5.3 |
| Lysozyme | 10 | KVYGRCELAAAMKRLGLDNFRGYSLGNWVCAA KFESNFNTHATNRNTDGSTDYGILQINSRWWC NDGRTPGSRNLCNIPCSALLSSDTIASVNCAK KIVSDGNGMNAWVAWRKRCKGTDVAWTRGCRL | 22 | 129 | 9.4 |

Table 6 shows the dissociation rate constant $k_{off}$, the maximum layer thickness change amount $\Delta\lambda$ and the b value regarding each of the peptides.

TABLE 6

| Peptide | $K_{off} \times 10^{-3}$ (sec$^{-1}$) | $\Delta\lambda$ (nm) | b value |
|---|---|---|---|
| (His) 3 | 2.57 | 0.027 | 0.344 |
| Bradykinin | 17.21 | 0.079 | 0.107 |
| (His) 10 | 0.73 | 0.086 | 0.093 |
| (Lys) 10 | 0.2 | 0.045 | 0.669 |
| (Glu) 10 | 0.69 | 0.041 | 0.069 |
| ELN 11mer | 0.16 | 0.043 | 0 |
| IS 13mer | 17.08 | 0.061 | 0.756 |
| Dynorphin A | 6.17 | 0.095 | 0.148 |
| ACTH15 | 11.47 | 0.061 | 0.029 |
| Kininogen | 4.93 | 0.082 | 1.093 |
| AB40 | 10.16 | 0.123 | 0.841 |
| AB42 | 0.15 | 0.079 | 0.09 |
| Lysozyme | 6.6 | 0.12 | 0.278 |

The results in Table 6 indicate that it is possible to measure and calculate the dissociation rate constant $k_{off}$, the maximum layer thickness change amount $\Delta\lambda$ and the b value regarding peptides having various amino acid residues. These results suggest that when first to third information on an unknown target peptide is obtained, the type of the target peptide can be easily determined by comparing the information to each value shown in Table 6.

EXPLANATION OF SEQUENCES LISTED IN SEQUENCE LIST

SEQ ID NO: 9 is a sequence of Arg-decapeptide.
SEQ ID NO: 10 is a sequence of His-eicosa-peptide.
SEQ ID NO: 18 is a sequence of His-decapeptide.
SEQ ID NO: 18 is a sequence of Lys-decapeptide.
SEQ ID NO: 20 is a sequence of Glu-decapeptide.

[Sequence List]

The invention claimed is:

1. A method for determining a type of target peptide comprising:
   (a) flowing a liquid containing a protein capable of binding to a target peptide onto a sensor chip, thereby directly immobilizing the protein on a surface of the sensor chip without using an adhesive between the surface of the sensor chip and the protein;
   (b) flowing a test sample containing the target peptide onto the sensor chip so as to form a complex of the target peptide and the protein on the sensor chip;
   (c) obtaining a maximum value of a layer thickness change amount on the sensor chip by measuring (i) changes in the layer thickness on a surface of the sensor chip in response to the target peptide binding to the protein, (ii) changes in the layer thickness on the surface of the sensor chip in response to the target peptide dissociating from the protein, or (iii) both of the changes (i) and (ii), by reflection interference spectroscopy;
   (d) obtaining a dissociation rate constant of the target peptide in response to the target peptide dissociating from the protein by measuring changes in the layer thickness on the surface of the sensor chip, by the reflection interference spectroscopy;
   (e) determining that a dissociation mode of the target peptide and the protein is either a single dissociation mode or a multiple dissociation mode;
   (f) comparing the dissociation rate constant of the target peptide, the maximum value of the layer thickness change amount, and the dissociation mode with a dissociation rate constant, a maximum value of a layer thickness change amount, and a dissociation mode which are previously measured using a reference peptide in a manner similar to the target peptide; and
   (g) determining whether or not the target peptide is the reference peptide based on a comparison result in the step (f),
   wherein the sensor chip comprises a silicon nitride substrate.

2. The method according to claim 1, wherein, in the step (e), the dissociation mode is determined based on a coefficient of an equation representing an approximate curve that is obtained by a least square method from a sensorgram after a time when the layer thickness change amount has reached the maximum value.

3. The method according to claim 2, wherein the equation representing the approximate curve is represented by the following Equation (I):

$$\Delta\lambda = a \times e^{-k_1 \cdot t} b \times e^{-k_2 \cdot t} \qquad (I)$$

(wherein, $\Delta\lambda$ represents a layer thickness change amount, a, b, $k_1$, and $k_2$ represent any numbers determined by curve fitting, and t represents elapsed time).

4. The method according to claim 3, wherein
in the step (d), when the b value in Equation (I) is lower than a predetermined threshold for classifying the dissociation mode into the single dissociation mode and the multiple dissociation mode, the dissociation mode of the target peptide from the protein is determined to be the single dissociation mode, and
when the b value in Equation (I) is the threshold or more, the dissociation mode of the target peptide from the protein is determined to be the multiple dissociation mode.

5. The method according to claim 4, wherein the b value is set in a range between 0.109 and 0.519.

6. The method according to claim 1, wherein the protein is a protein present in blood.

7. The method according to claim 1, wherein the protein is at least one of albumin, transthyretin, and globulin.

8. The method according to claim 1, wherein
in the step (f), the dissociation rate constant, the maximum value of the layer thickness change amount, and the dissociation mode of each of the multiple types of reference peptides are used, and
in the step (g), whether or not the target peptide is any one of the multiple types of reference peptides is determined based on the comparison result obtained in the step (f).

9. The method according to claim 1, wherein the test sample is collected from a living body.

10. The method according to claim 1, wherein the protein immobilized on the sensor chip is one selected from the group consisting of: human serum albumin (HSA), one protein among a plurality of types of protein in human whole blood, human γ-globulin (HyG), transthyretin, bovine serum albumin (BSA), and heat-denatured BSA.

11. A method for determining a type of target peptide comprising:
(a) flowing a liquid containing a protein capable of binding to a target peptide onto a sensor chip, thereby immobilizing the protein on a surface of the sensor chip by physisorption;
(b) flowing a test sample containing the target peptide onto the sensor chip so as to form a complex of the target peptide and the protein on the sensor chip;
(c) obtaining a maximum value of a layer thickness change amount on the sensor chip by measuring (i) changes in the layer thickness on a surface of the sensor chip in response to the target peptide binding to the protein, (ii) changes in the layer thickness on the surface of the sensor chip in response to the target peptide dissociating from the protein, or (iii) both of the changes (i) and (ii), by reflection interference spectroscopy;
(d) obtaining a dissociation rate constant of the target peptide in response to the target peptide dissociating from the protein by measuring changes in the layer thickness on the surface of the sensor chip, by the reflection interference spectroscopy;
(e) determining that a dissociation mode of the target peptide and the protein is either a single dissociation mode or a multiple dissociation mode;
(f) comparing the dissociation rate constant of the target peptide, the maximum value of the layer thickness change amount, and the dissociation mode with a dissociation rate constant, a maximum value of a layer thickness change amount, and a dissociation mode which are previously measured using a reference peptide in a manner similar to the target peptide; and
(g) determining whether or not the target peptide is the reference peptide based on a comparison result in the step (f),
wherein the sensor chip comprises a silicon nitride substrate.

* * * * *

```
                       SEQUENCE LISTING

<160> NUMBER OF SEQ ID NOS: 22

<210> SEQ ID NO 1
<211> LENGTH: 24
<212> TYPE: PRT
<213> ORGANISM: Homo sapiens

<400> SEQUENCE: 1

Ser Tyr Ser Met Glu His Phe Arg Trp Gly Lys Pro Val Gly Lys Lys
1               5                   10                  15

Arg Arg Pro Val Lys Val Tyr Pro
            20

<210> SEQ ID NO 2
<211> LENGTH: 39
<212> TYPE: PRT
<213> ORGANISM: Homo sapiens

<400> SEQUENCE: 2

Ser Tyr Ser Met Glu His Phe Arg Trp Gly Lys Pro Val Gly Lys Lys
1               5                   10                  15

Arg Arg Pro Val Lys Val Tyr Pro Asn Ala Gly Glu Asn Glu Ser Ala
            20                  25                  30

Glu Ala Phe Pro Leu Glu Phe
            35

<210> SEQ ID NO 3
<211> LENGTH: 41
```

```
<212> TYPE: PRT
<213> ORGANISM: Homo sapiens

<400> SEQUENCE: 3

Gly Pro Ser Tyr Ser Met Glu His Phe Arg Trp Gly Lys Pro Val Gly
1               5                   10                  15

Lys Lys Arg Arg Pro Val Lys Val Tyr Pro Asn Gly Ala Glu Asp Glu
            20                  25                  30

Ser Ala Glu Ala Phe Pro Leu Glu Phe
        35                  40

<210> SEQ ID NO 4
<211> LENGTH: 18
<212> TYPE: PRT
<213> ORGANISM: Homo sapiens

<400> SEQUENCE: 4

Arg Leu Ile Glu Asp Ile Cys Leu Pro Arg Trp Gly Cys Leu Trp Glu
1               5                   10                  15

Asp Asp

<210> SEQ ID NO 5
<211> LENGTH: 32
<212> TYPE: PRT
<213> ORGANISM: Homo sapiens

<400> SEQUENCE: 5

Gly Glu Ser Arg Asn Arg Asn Val His Ser Gly Ser Thr Phe Phe Lys
1               5                   10                  15

Tyr Tyr Leu Gln Gly Ala Lys Ile Pro Lys Pro Glu Ala Ser Phe Ser
            20                  25                  30

<210> SEQ ID NO 6
<211> LENGTH: 29
<212> TYPE: PRT
<213> ORGANISM: Homo sapiens

<400> SEQUENCE: 6

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr
            20                  25

<210> SEQ ID NO 7
<211> LENGTH: 32
<212> TYPE: PRT
<213> ORGANISM: Homo sapiens

<400> SEQUENCE: 7

Ser Pro Lys Met Val Gln Gly Ser Gly Cys Phe Gly Arg Lys Met Asp
1               5                   10                  15

Arg Ile Ser Ser Ser Ser Gly Leu Gly Cys Lys Val Leu Arg Arg His
            20                  25                  30

<210> SEQ ID NO 8
<211> LENGTH: 25
<212> TYPE: PRT
<213> ORGANISM: Homo sapiens

<400> SEQUENCE: 8

Asp Glu Ala Gly Ser Glu Ala Asp His Glu Gly Thr His Ser Thr Lys
1               5                   10                  15
```

-continued

```
Arg Gly His Ala Lys Ser Arg Pro Val
            20              25

<210> SEQ ID NO 9
<211> LENGTH: 10
<212> TYPE: PRT
<213> ORGANISM: Artificial Sequence
<220> FEATURE:
<223> OTHER INFORMATION: Synthetic Arg decapeptide

<400> SEQUENCE: 9

Arg Arg Arg Arg Arg Arg Arg Arg Arg Arg
1               5                   10

<210> SEQ ID NO 10
<211> LENGTH: 20
<212> TYPE: PRT
<213> ORGANISM: Artificial Sequence
<220> FEATURE:
<223> OTHER INFORMATION: Synthetic His eicosapeptide

<400> SEQUENCE: 10

His His His His His His His His His His His His His His His
1               5                   10                  15

His His His His
            20

<210> SEQ ID NO 11
<211> LENGTH: 15
<212> TYPE: PRT
<213> ORGANISM: Homo sapiens

<400> SEQUENCE: 11

Tyr Ser Met Glu His Phe Arg Trp Gly Lys Pro Val Gly Lys Lys
1               5                   10                  15

<210> SEQ ID NO 12
<211> LENGTH: 40
<212> TYPE: PRT
<213> ORGANISM: Homo sapiens

<400> SEQUENCE: 12

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val
            35                  40

<210> SEQ ID NO 13
<211> LENGTH: 42
<212> TYPE: PRT
<213> ORGANISM: Homo sapiens

<400> SEQUENCE: 13

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val Ile Ala
            35                  40
```

```
<210> SEQ ID NO 14
<211> LENGTH: 13
<212> TYPE: PRT
<213> ORGANISM: Homo sapiens

<400> SEQUENCE: 14

Tyr Gly Gly Phe Leu Arg Arg Ile Arg Pro Lys Leu Lys
1               5                   10

<210> SEQ ID NO 15
<211> LENGTH: 19
<212> TYPE: PRT
<213> ORGANISM: Homo sapiens

<400> SEQUENCE: 15

His Asn Leu Gly His Gly His Lys His Glu Arg Asp Gln Gly His Gly
1               5                   10                  15

His Gln Arg

<210> SEQ ID NO 16
<211> LENGTH: 9
<212> TYPE: PRT
<213> ORGANISM: Homo sapiens

<400> SEQUENCE: 16

Arg Pro Pro Gly Phe Ser Pro Phe Arg
1               5

<210> SEQ ID NO 17
<211> LENGTH: 10
<212> TYPE: PRT
<213> ORGANISM: Artificial Sequence
<220> FEATURE:
<223> OTHER INFORMATION: Synthetic His decapeptide

<400> SEQUENCE: 17

His His His His His His His His His His
1               5                   10

<210> SEQ ID NO 18
<211> LENGTH: 10
<212> TYPE: PRT
<213> ORGANISM: Artificial Sequence
<220> FEATURE:
<223> OTHER INFORMATION: Synthetic Lys decapeptide

<400> SEQUENCE: 18

Lys Lys Lys Lys Lys Lys Lys Lys Lys Lys
1               5                   10

<210> SEQ ID NO 19
<211> LENGTH: 10
<212> TYPE: PRT
<213> ORGANISM: Artificial Sequence
<220> FEATURE:
<223> OTHER INFORMATION: Synthetic Glu decapeptide

<400> SEQUENCE: 19

Glu Glu Glu Glu Glu Glu Glu Glu Glu Glu
1               5                   10

<210> SEQ ID NO 20
<211> LENGTH: 11
<212> TYPE: PRT
<213> ORGANISM: Homo sapiens
```

```
<400> SEQUENCE: 20

Gly Val Pro Gly Leu Gly Val Gly Ala Gly Val
1               5                   10

<210> SEQ ID NO 21
<211> LENGTH: 13
<212> TYPE: PRT
<213> ORGANISM: Homo sapiens

<400> SEQUENCE: 21

Ala Trp Ala Val Ala Arg Leu Ser Gln Arg Phe Pro Lys
1               5                   10

<210> SEQ ID NO 22
<211> LENGTH: 129
<212> TYPE: PRT
<213> ORGANISM: Homo sapiens

<400> SEQUENCE: 22

Lys Val Tyr Gly Arg Cys Glu Leu Ala Ala Met Lys Arg Leu Gly
1               5                   10                  15

Leu Asp Asn Phe Arg Gly Tyr Ser Leu Gly Asn Trp Val Cys Ala Ala
                20                  25                  30

Lys Phe Glu Ser Asn Phe Asn Thr His Ala Thr Asn Arg Asn Thr Asp
            35                  40                  45

Gly Ser Thr Asp Tyr Gly Ile Leu Gln Ile Asn Ser Arg Trp Trp Cys
        50                  55                  60

Asn Asp Gly Arg Thr Pro Gly Ser Arg Asn Leu Cys Asn Ile Pro Cys
65                  70                  75                  80

Ser Ala Leu Leu Ser Ser Asp Thr Ile Ala Ser Val Asn Cys Ala Lys
                85                  90                  95

Lys Ile Val Ser Asp Gly Asn Gly Met Asn Ala Trp Val Ala Trp Arg
                100                 105                 110

Lys Arg Cys Lys Gly Thr Asp Val Asn Ala Trp Thr Arg Gly Cys Arg
            115                 120                 125

Leu
```